(12) United States Patent
Lear et al.

(10) Patent No.: US 11,612,388 B2
(45) Date of Patent: Mar. 28, 2023

(54) HEMI-BRIDGE AND METHODS OF MANUFACTURING AND USING SAME

(71) Applicant: SUTUREGARD Medical, Inc., Portland, OR (US)

(72) Inventors: William Lear, Corvallis, OR (US); Daniel A Ladizinsky, Lake Oswego, OR (US); Jennifer Akeroyd, Corvallis, OR (US)

(73) Assignee: SUTUREGARD Medical Inc., Corvallis, OR (US)

( * ) Notice: Subject to any disclaimer, the term of this patent is extended or adjusted under 35 U.S.C. 154(b) by 357 days.

(21) Appl. No.: 16/879,971

(22) Filed: May 21, 2020

(65) Prior Publication Data

US 2020/0330089 A1     Oct. 22, 2020

Related U.S. Application Data

(63) Continuation-in-part of application No. 16/576,907, filed on Sep. 20, 2019, now Pat. No. 10,702,262.

(60) Provisional application No. 62/876,849, filed on Jul. 22, 2019, provisional application No. 62/836,341, filed on Apr. 19, 2019.

(51) Int. Cl.
    *A61B 17/04*     (2006.01)

(52) U.S. Cl.
    CPC ............................... *A61B 17/0466* (2013.01)

(58) Field of Classification Search
    CPC ...... A61B 17/0466; A61B 2017/00526; A61B 2017/0495; A61B 2017/086
    See application file for complete search history.

(56) References Cited

U.S. PATENT DOCUMENTS

| | | | | |
|---|---|---|---|---|
| 3,664,345 A * | 5/1972 | Dabbs | ............... | A61B 17/0401 606/232 |
| 4,881,546 A * | 11/1989 | Kaessmann | .......... | A61B 17/085 606/217 |
| 6,254,624 B1 * | 7/2001 | Oddsen | .................. | A61B 90/02 606/216 |
| 2002/0198565 A1 * | 12/2002 | Dominguez | ....... | A61B 17/0466 606/228 |
| 2003/0078617 A1 * | 4/2003 | Schwartz | ............ | A61L 27/3852 606/232 |
| 2006/0064125 A1 * | 3/2006 | Henderson | ........... | A61B 17/085 606/215 |
| 2016/0143638 A1 * | 5/2016 | Renke | .................. | A61B 17/085 606/215 |

* cited by examiner

*Primary Examiner* — Richard G Louis
(74) *Attorney, Agent, or Firm* — Wei & Sleman LLP

(57) ABSTRACT

A suture securing device having a plurality of zones includes a first zone, a second zone and a third zone. The device includes a lower layer extending across each of the first zone, the second zone and the third zone, an upper layer disposed in the first zone and the second zone, and an insert having at least one eyelet disposed in the first zone, the insert being sandwiched between the upper layer and the lower layer.

17 Claims, 22 Drawing Sheets

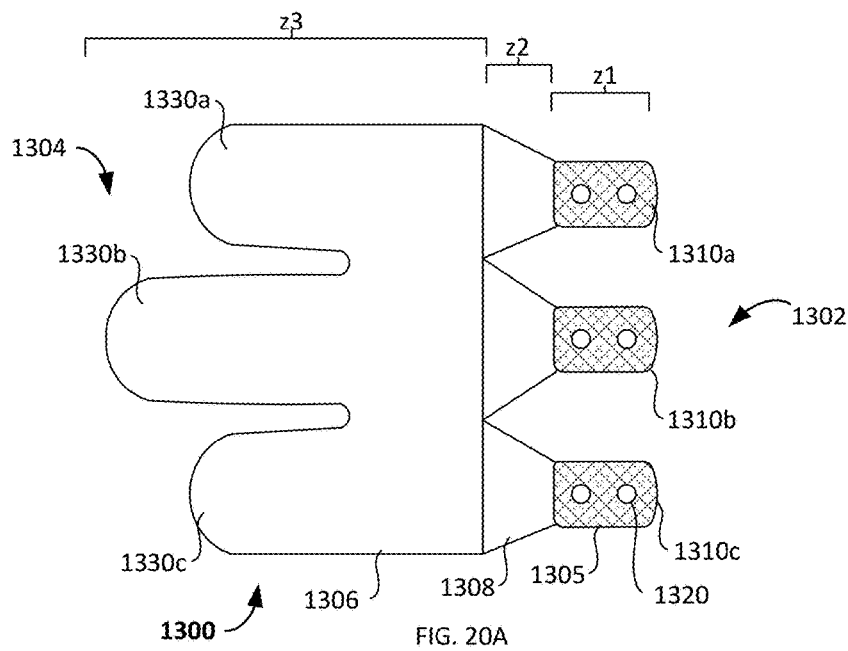
FIG. 20A
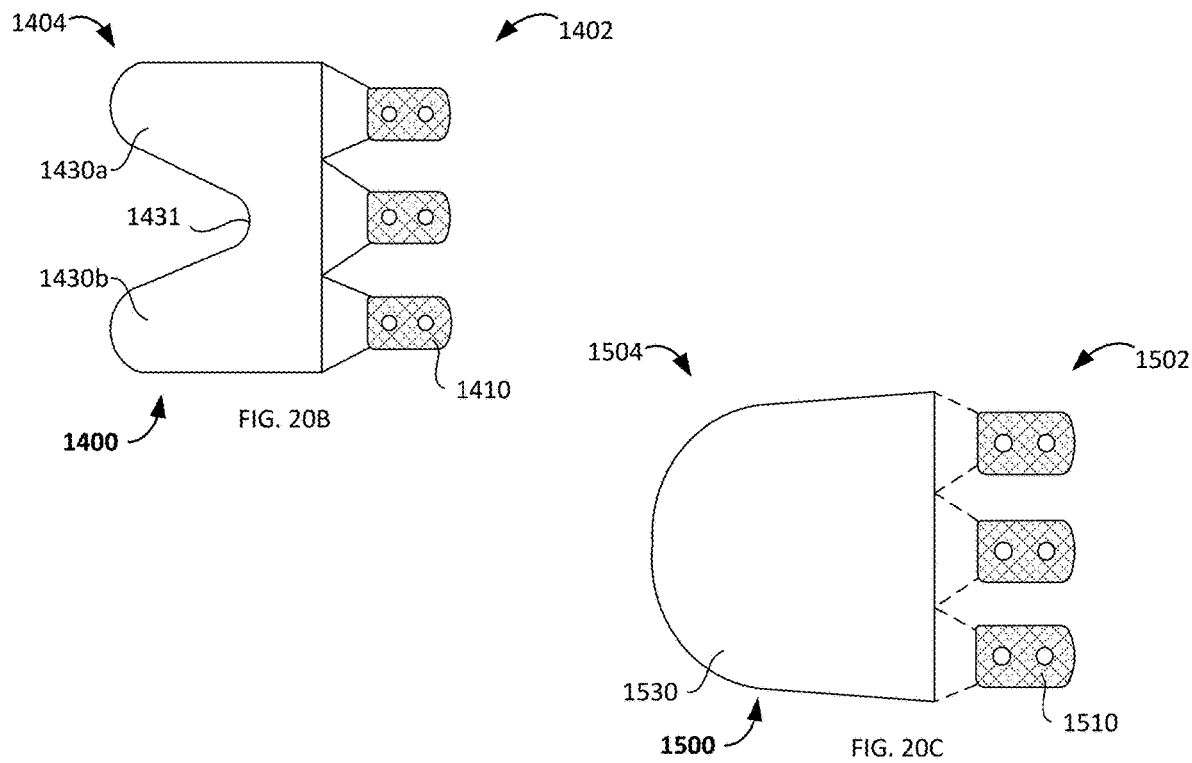
FIG. 20B
FIG. 20C

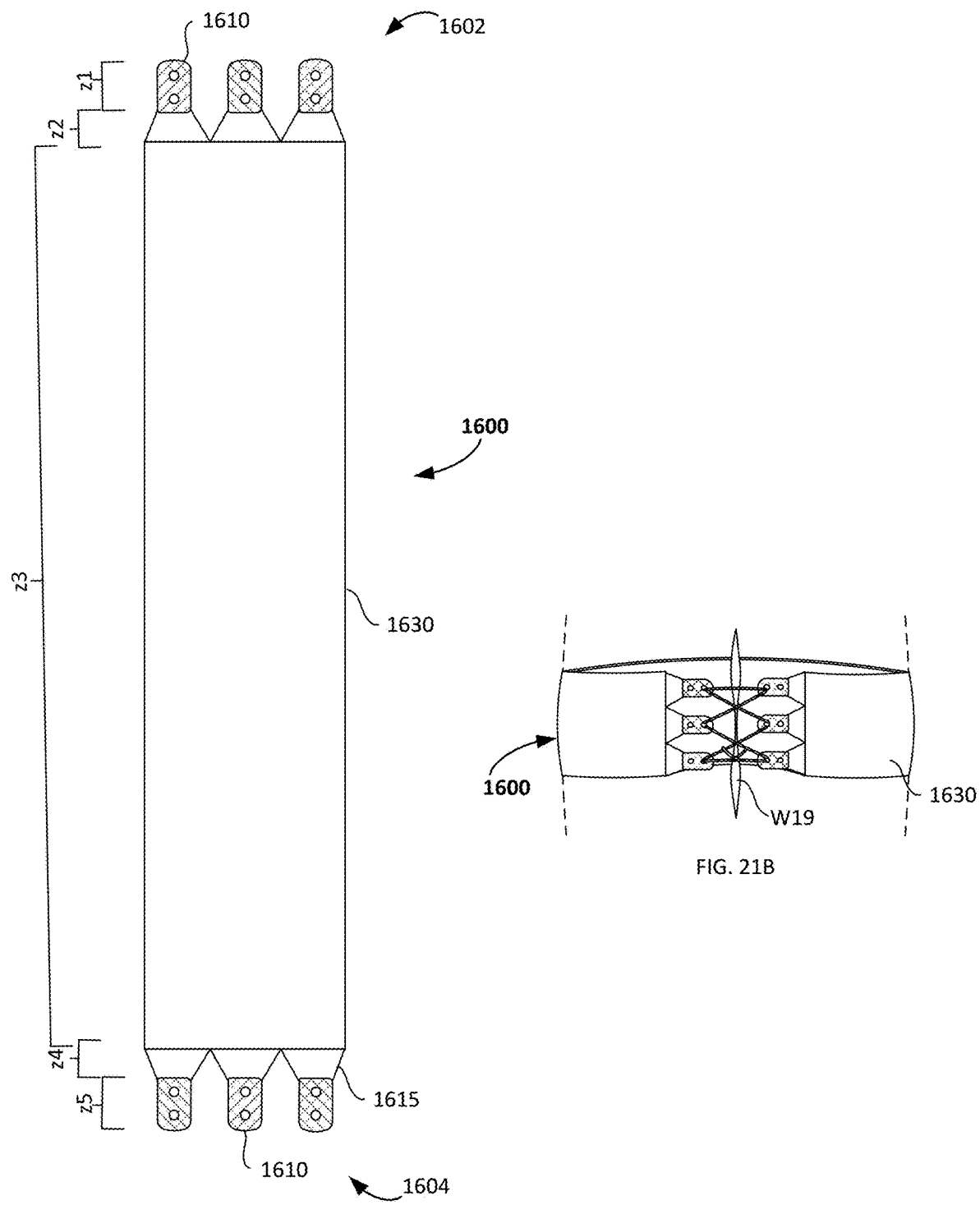

HEMI-BRIDGE AND METHODS OF MANUFACTURING AND USING SAME

CROSS-REFERENCE TO RELATED APPLICATIONS

This application is a continuation-in-part of U.S. Non-Provisional application Ser. No. 16/576,907, which claims priority to U.S. Provisional Application Ser. No. 62/876,849, filed Jul. 22, 2019, and U.S. Provisional Application Ser. No. 62/836,341, filed Apr. 19, 2019, the contents of which are hereby incorporated by reference in their entirety as if fully set forth herein.

FIELD OF THE DISCLOSURE

The present disclosure relates generally to wound closure and methods and devices for improving same. More specifically, the present disclosure relates to a hemi-bridge device and methods for facilitating wound closure using same.

BACKGROUND OF THE DISCLOSURE

Sutures are stitches used to close open wounds and/or surgical incisions of a patient. A medical practitioner generally uses a needle with an attached thread to substantially sew two adjacent sections of skin together to close the wound or incision. Surgical knots are often used to secure the sutures and ensure proper healing. Sutures and surgical knots contacting the skin can be inflammatory and/or become "ingrown" and actually impede healing of the wound or incision. Additionally, complications may arise if the suture is tied too tightly or too loosely. Moreover, traditional techniques may leave unsightly "track marks."

Closure may be difficult, especially in high-tension areas of the skin, such where skin overlies the shoulder, knee, angle of the mandible, etc. Wound eversion occurs when the two wound surfaces are horizontally opposed into one another such that the closed incision is under no tension and topographically lies in a plane above the resting horizontal skin plane. Wound closures with maximal eversion resist excessive widening of the scar due to ongoing ambient stresses in the high-tension area during the wound healing and scar maturation processes. However, wound eversion can be technically difficult to achieve for less skilled operator, and a device to facilitate this is desirable. Further, there may be excessive tension on closures where an excisional defect is present in the skin. When suture is placed under excessive tension to close such wounds, the suture itself can slice through the skin ("cheesewiring").

Moreover, adhesive dressings of uniform elasticity impart shear force to the skin, greatest at the point of the dressing farthest from the source of the tension, which increases the risk of blistering. There is a need for an adhesive dressing of variable elasticity such that the elasticity at the end of the dressing farthest from the source of tension moves with a skin-like elasticity and thus reduces the risk of blistering.

Thus, there exists a need for suture devices that improve upon and advance the known suturing and dressing techniques.

SUMMARY OF THE DISCLOSURE

In at least some embodiments, a stress dispersing device having a plurality of zones including a first zone, a second zone and a third zone, includes a lower layer extending across each of the first zone, the second zone and the third zone, an upper layer disposed in the first zone and the second zone, and an insert having at least one eyelet disposed in the first zone, the insert being sandwiched between the upper layer and the lower layer.

In some embodiments, a stress dispersing device having a plurality of zones including a first zone, a second zone, a third zone, a fourth zone, and a fifth zone includes a lower layer extending across each of the plurality of zones, an upper layer disposed in the first zone, the second zone, the fourth zone, and the fifth zone, and at least one insert having at least one eyelet disposed in the first zone and the fifth zone, the at least one insert being sandwiched between the upper layer and the lower layer.

In at least some embodiments, a system includes a suture securing device including a pair of hemi-bridges, each of the pair of hemi-bridges having a plurality of zones including a first zone, a second zone and a third zone, the hemi-bridges including (i) a lower layer extending across each of the first zone, the second zone and the third zone, (ii) an upper layer disposed in the first zone and the second zone, and (iii) an insert having at least one eyelet disposed in the first zone, the insert being sandwiched between the upper layer and the lower layer; and a fastening element coupling the pair of hemi-bridges.

BRIEF DESCRIPTION OF THE DISCLOSURE

Various embodiments of the presently disclosed hemi-bridges are disclosed herein with reference to the drawings, wherein.

Figure 5A:
Figure 5B:
Figure 5C:
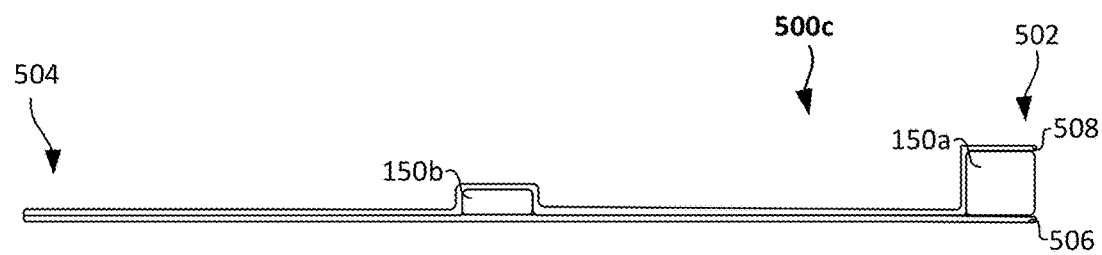
Figure 6:
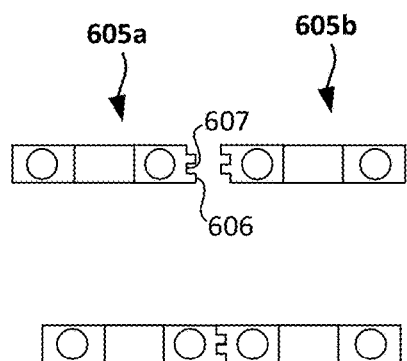
Figure 7:
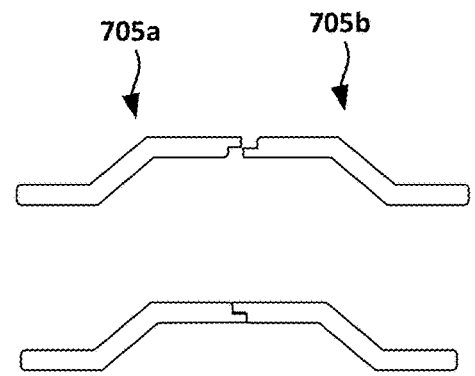
Figure 8:
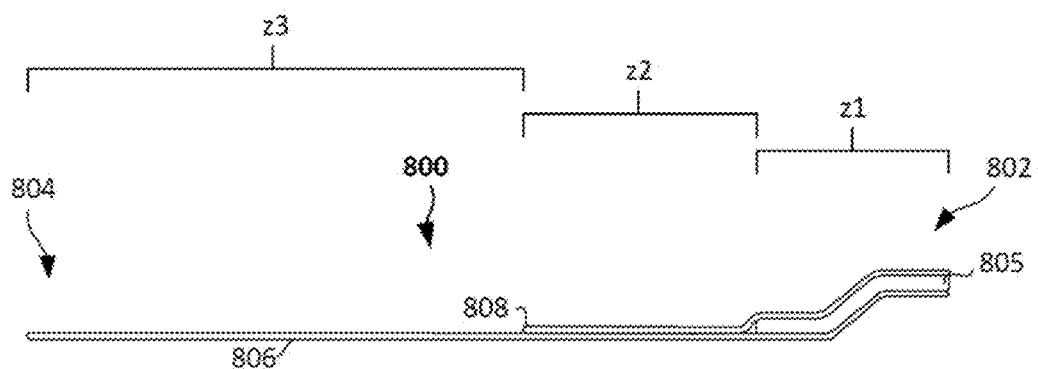
Figure 9:
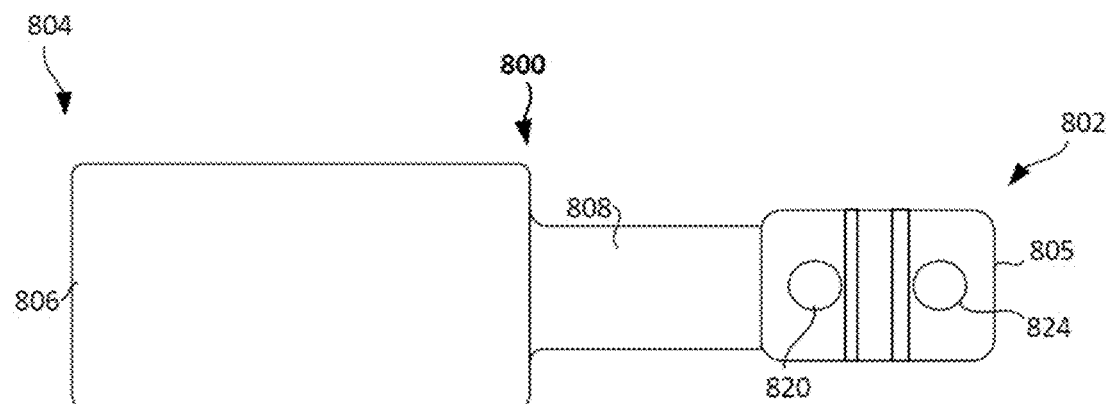
Figure 10:
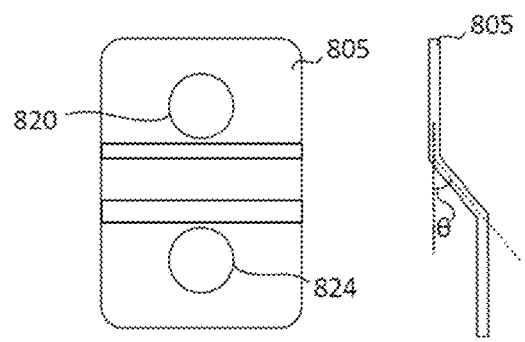
Figure 11:
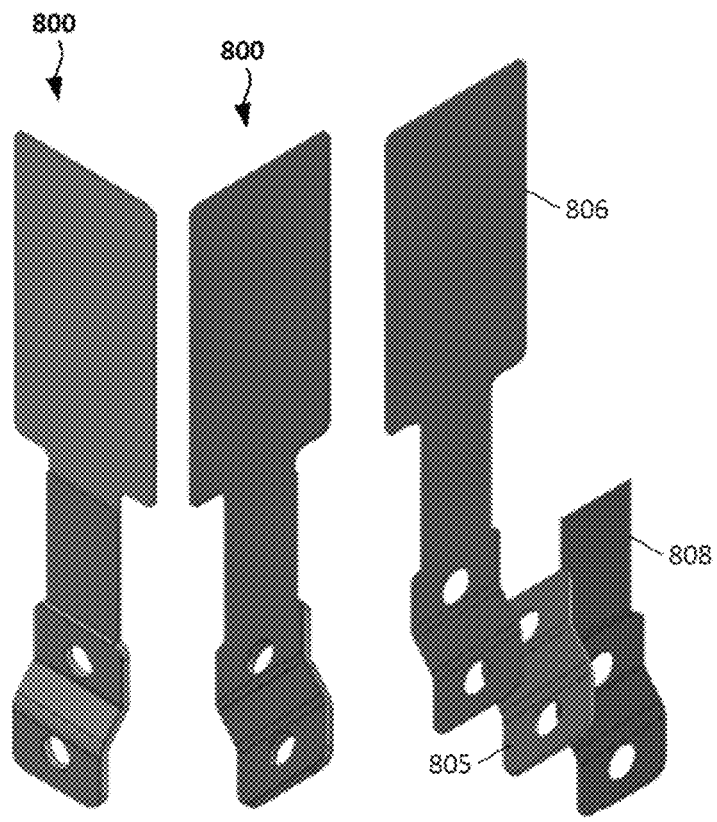
Figure 12:
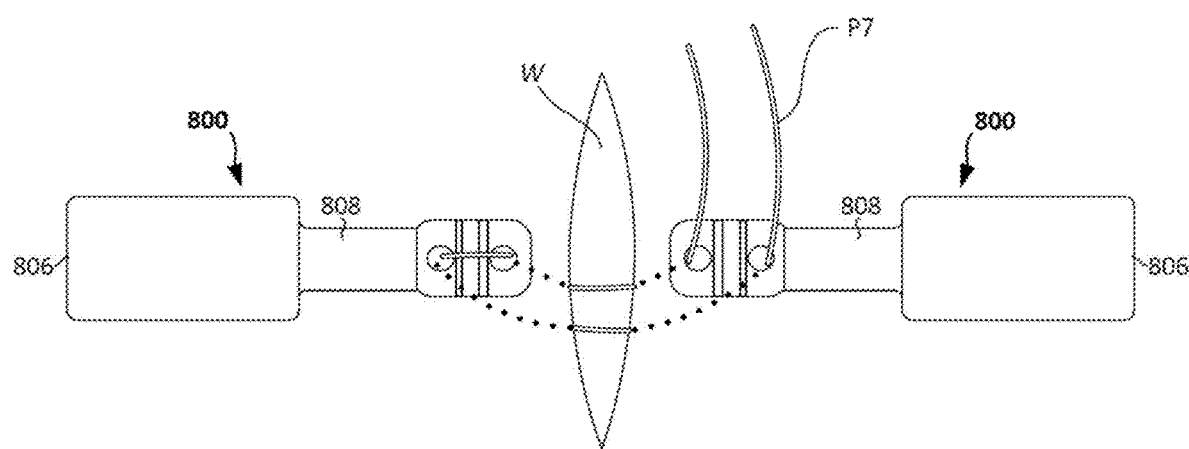
Figure 13A:
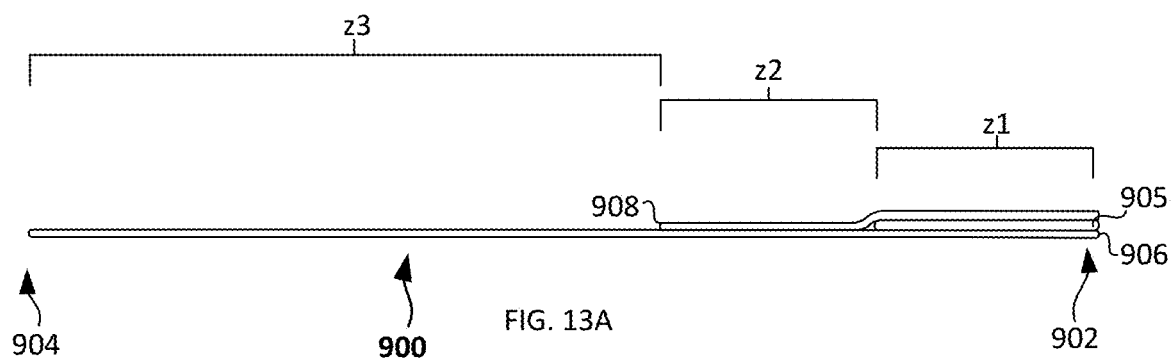
Figure 13B:
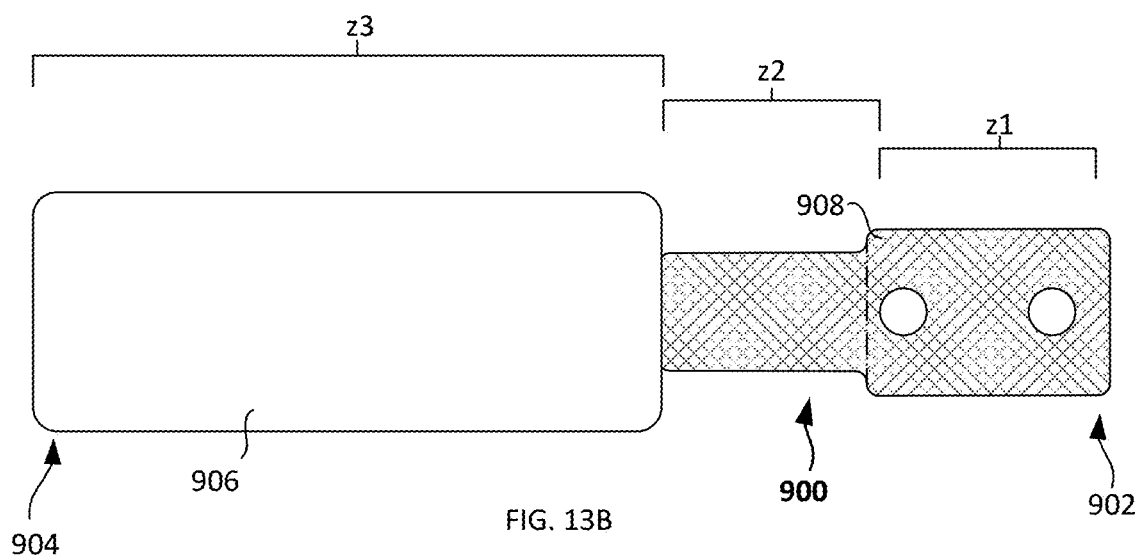
Figure 14A:
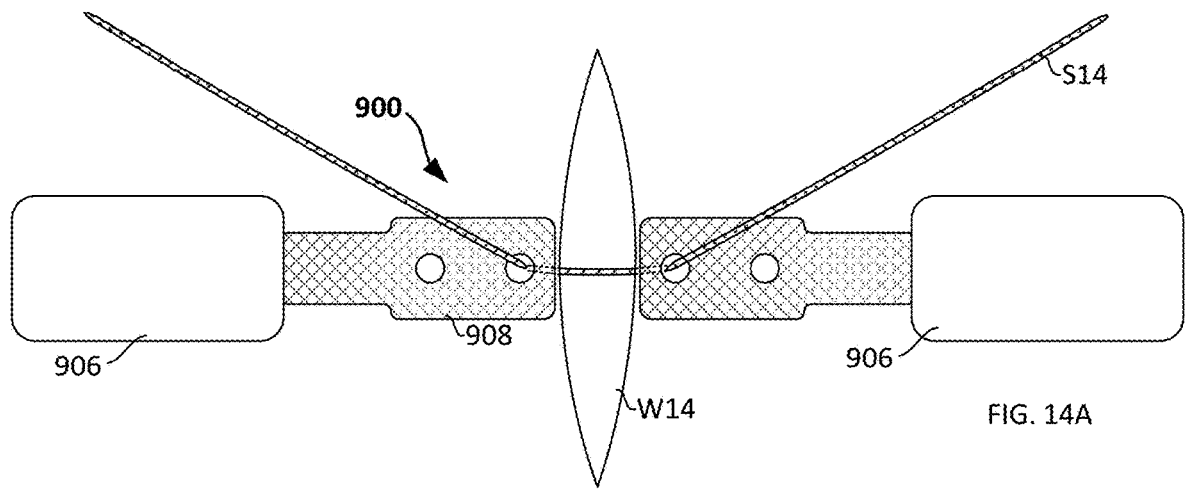
Figure 14B:
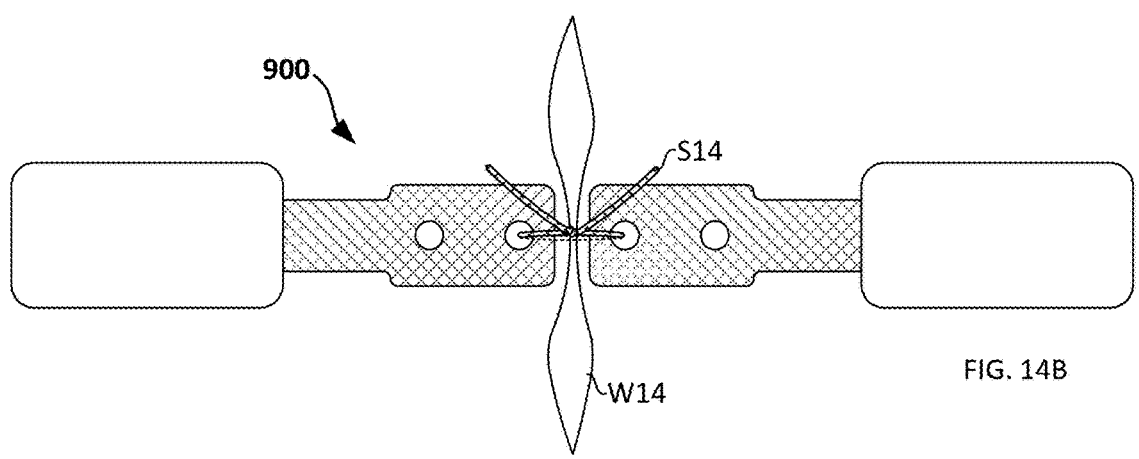
Figure 14C:
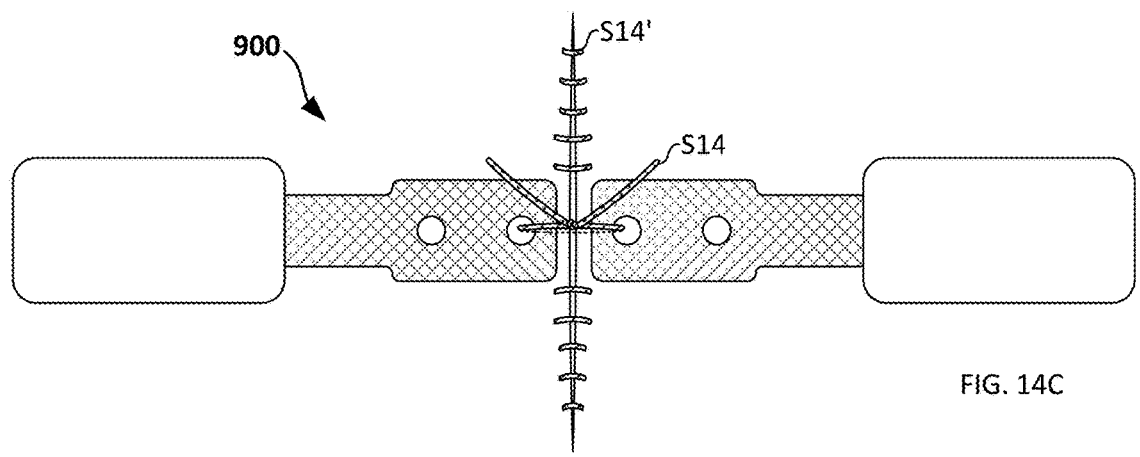
Figure 14D:
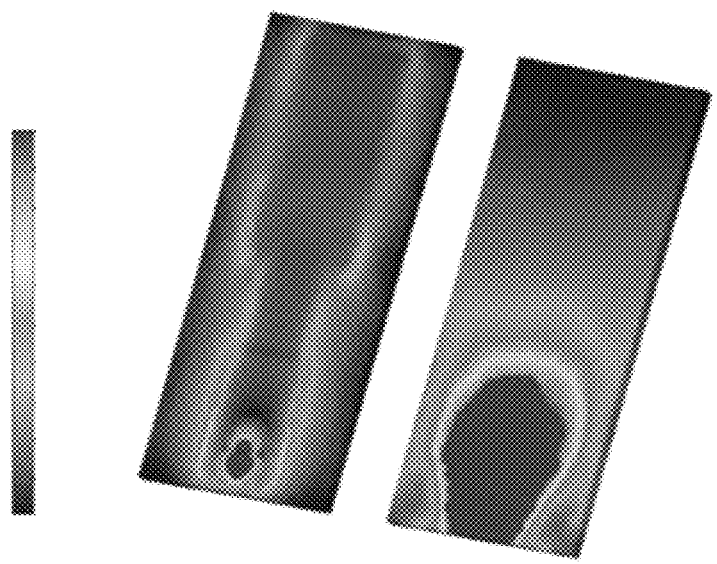
Figure 15A:
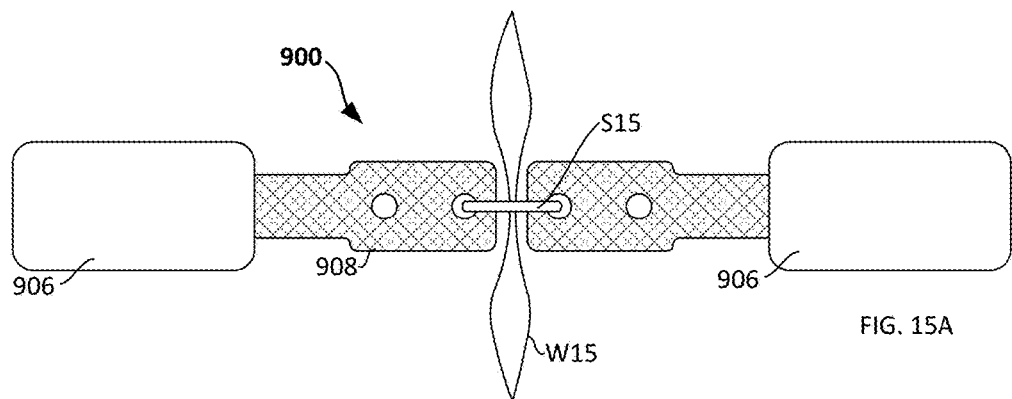
Figure 15B:
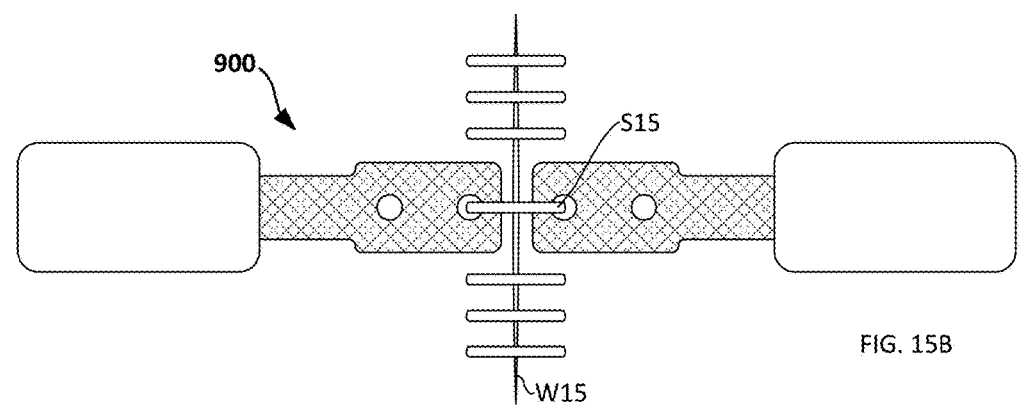
Figure 15C:
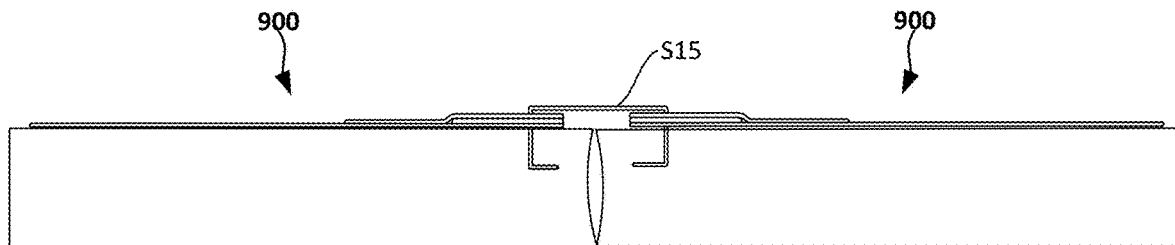
Figure 16A:
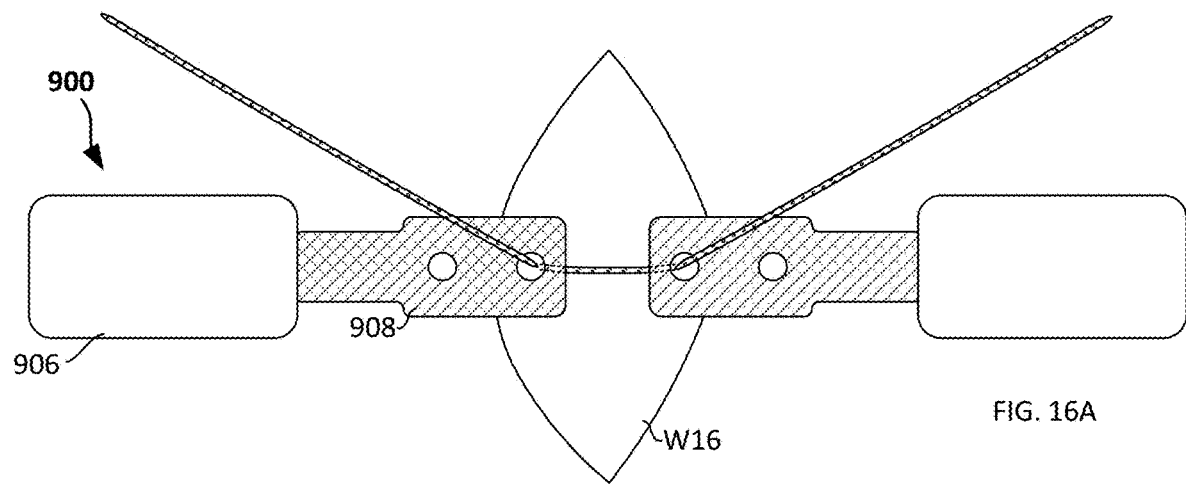
Figure 16B:
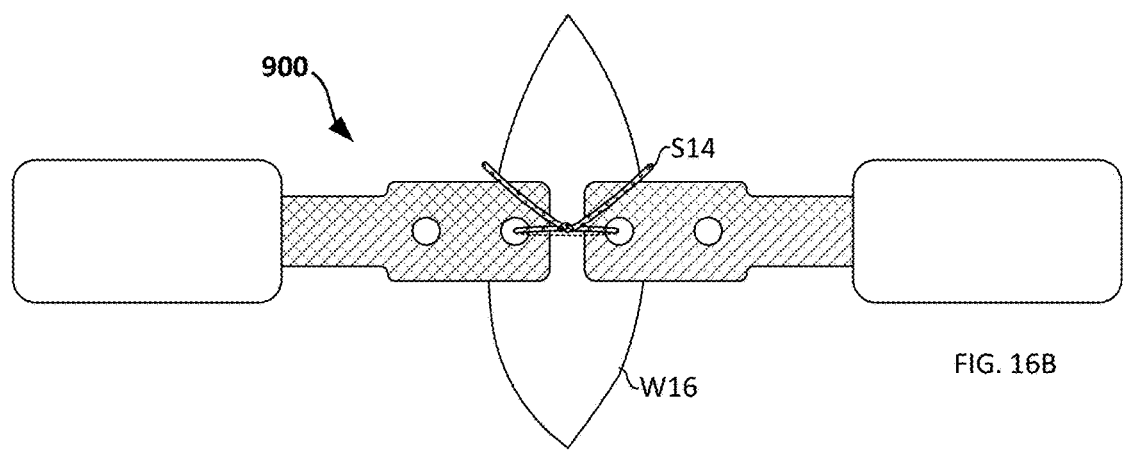
Figure 18A:
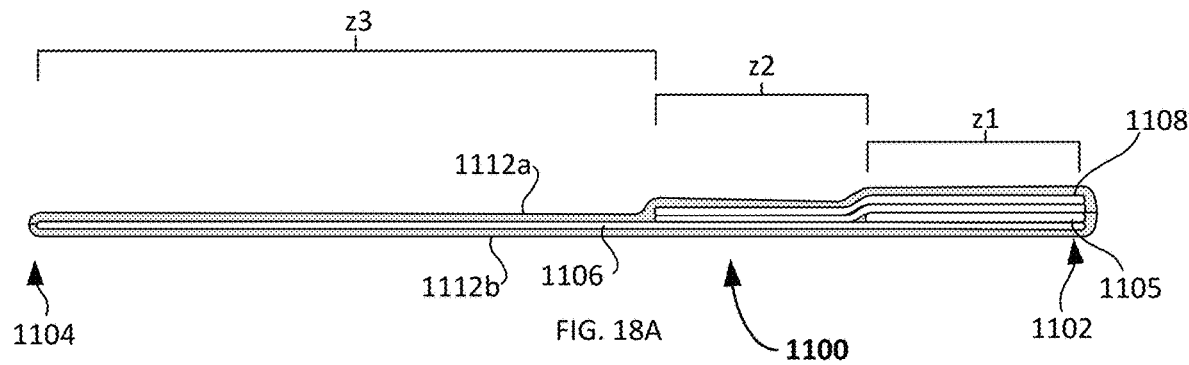
Figure 18B:
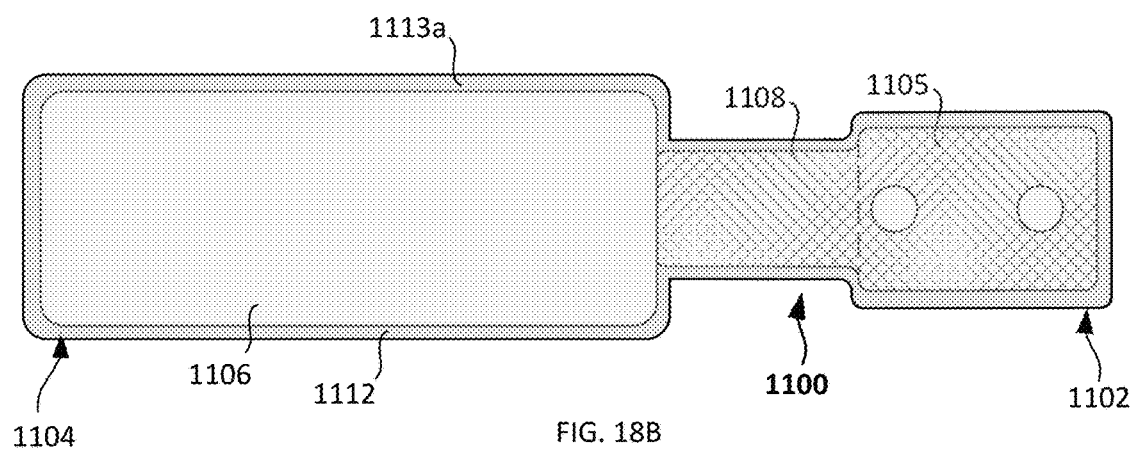
Figure 18C:
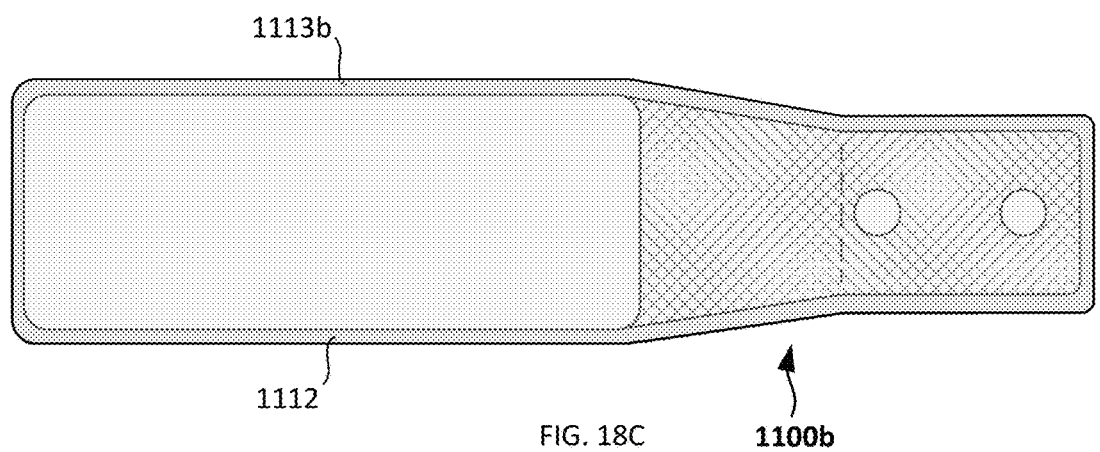
Figure 22A:
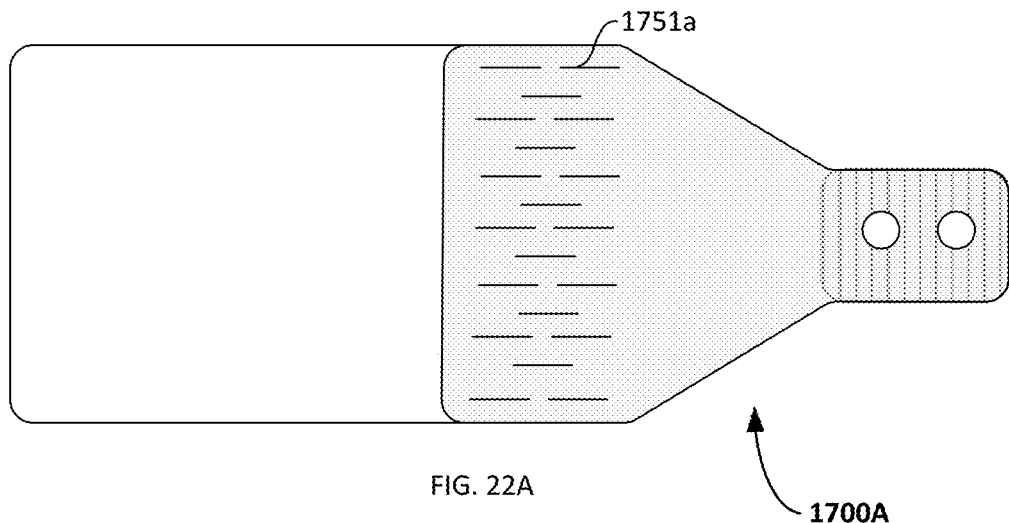
Figure 22B:
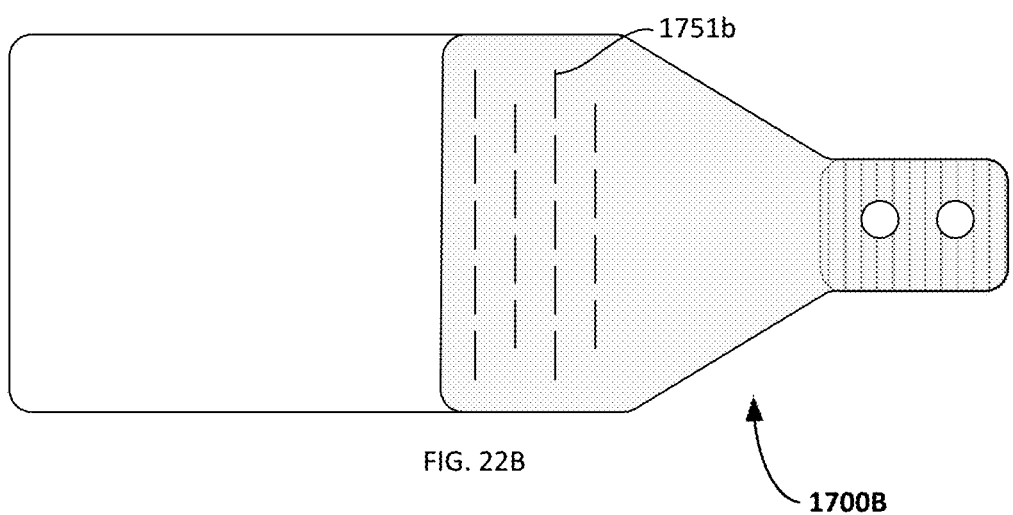
Figure 22C:
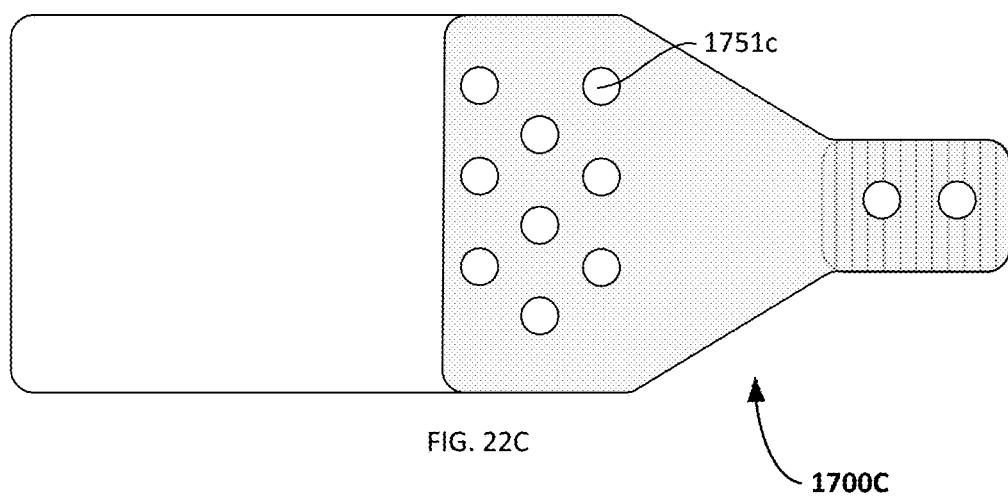

FIGS. 4A-F are schematic illustrations showing various suture patterns;

FIGS. 5A-C are alternative embodiments of a hemi-bridge having inserts of various shapes;

FIGS. 6-7 are schematic top and side views of variations of hemi-bridges having interdigitation features;

FIGS. 8 and 9 are schematic illustrations showing side and top views of a hemi-bridge according to yet another embodiment;

FIG. 10 is schematic top and side views of the insert of the hemi-bridge of FIGS. 8 and 9;

FIG. 11 includes perspective top and bottom views of the hemi-bridge of FIGS. 8 and 9, and a third perspective exploded view of the components of the hemi-bridge;

FIG. 12 is a schematic illustration showing a pair of hemi-bridges being used with one possible suture pattern to close a wound;

FIGS. 13A-B are schematic illustrations showing a side view of a flat hemi-bridge, and a top view of the flat hemi-bridge according to yet another embodiment;

FIGS. 13C-F are schematic top and side views showings several variations of the flat hemi-bridge of FIGS. 13A-B;

FIGS. 14A-C are schematic illustrations showing the use of the flat hemi-bridge device of FIGS. 13A-B;

FIG. 14D is an illustration of a finite element analysis showing stress profiles of a wound closed with a hemi-bridge device, and a wound closed without a hemi-bridge device;

FIGS. 15A-C are schematic illustrations showing the use of the flat hemi-bridge device with staples;

FIGS. 16A-B illustrate another example of using a flat hemi-bridge device of FIGS. 13A-B;

FIGS. 17A-G are schematic top view and sides views of other embodiments of hemi-bridges having transitioning sections;

FIGS. 18A-C are schematic side and top views of another embodiment of a hemi-bridge having a waterproof coverings;

FIGS. 19A-D are schematic top views of several examples of eyelet arrangement on a hemi-bridge;

FIGS. 20A-F are schematic top views of several embodiments of hemi-bridges having a plurality of digits, and suture patterns to be used therewith;

FIGS. 21A-B are schematic top and perspective views of a unibody hemi-bridge having digits; and FIGS. 22A-C are schematic top views of several examples of a hemi-bridge having slits or holes in a second zone.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to wound closure devices, conventional methods suffer from some shortcomings as discussed above.

There therefore is a need for further improvements to the devices and methods used to help facilitate proper and quicker healing of a wound. Among other advantages, the present disclosure may address one or more of these needs.

Figure 1:
FIG. 1 is schematic cross-sectional view of a hemi-bridge according to one embodiment of the present disclosure.

FIG. 1 is schematic cross-sectional view of a hemi-bridge 100. Hemi-bridge 100 generally extends between a proximal end 102 and a distal end 104, the proximal end being relatively closer to the wound, and the distal end being relatively farther from the wound. Hemi-bridge may include an insert 105 sandwiched between two layers of material. As shown, the insert is sandwiched between two layers of material include a lower layer 106, and an upper layer 108. In some variations, one or more waterproof layers may be disposed above the upper or lower layers so that a total of two, three, or four layers may be formed, not including the insert.

Insert 105 may be formed of a rigid material. In some examples, the insert is formed of a thermoplastic material such as polypropylene, polyethylene terephthalate, polyethylene (LDPE and HDPE), polymethylmethacrylate, polyethylene terepthalate glycol (PTG) such as 10 MIL or 20 MIL PETG or as low as 1 MIL PETG, polydimethyl siloxane, polyoxymethylene, polycarbonate, polyamide and nylon, polyvinyl chloride, polyphenylene sulfide, acrylonitrilebutadienestyrene, polystyrene, polytetrafluoroethylene or polyurethane. Preferably the thermoplastic material may have a suitable melting temperatures. Insert 105 may be formed of other suitable materials such as metals.

Figure 2:
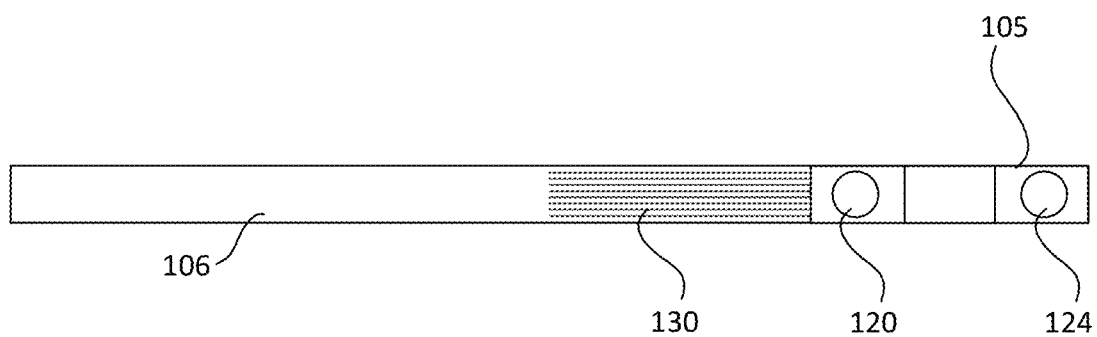
FIG. 2 is a schematic top view of the hemi-bridge of FIG. 1.

As shown, insert 105 may be stair-shaped, including a lower step 110, an inclined ramp 112 and an upper step 114, the inclined ramp connecting the two steps together. Insert 105 may have a length of approximately 5-20 mm, and preferably about 10 mm. Insert 105 may have a width that is approximately 2-6 mm, and a thickness of approximately 0.025 to 2 mm, depending on the material chosen. For example, a 20 MIL PETG insert may be 0.5 mm thick, a 10 MIL PETG insert may be 0.25 mm thick and a 1 MIL PETG insert may be 0.025 mm thick. In at least some examples, the upper step may be elevated by approximately 2 to 5 mm. In at least some examples, the lower and upper steps are of a same length, or approximately a same length. Insert 105 may have a generally constant single thickness along the lower step, the inclined ramp and the upper step. As best shown in FIG. 2, each of the upper and lower steps 110,114 may include a respective eyelet 120,124 for receiving a suture. In at least some examples, the eyelets are circular and of a same size as shown. Alternatively, eyelets may be formed of other shapes, such as oval, rectangular, triangular, etc. Eyelets 120,124 may allow the hemi-bridge to be used with various suturing configurations including simple, pulley and vertical mattress configurations, as will be described in more detail below. It will be understood that an insert may instead include only a single eyelet, or more than two eyelets (e.g., three, four, five or more eyelets).

Insert 105 may be disposed on one end of the device, in this case adjacent the proximal end 102, and may be substantially or entirely covered by lower and upper layers 106,108. Lower and upper layers 106,108 may be formed of rectangular strips of material, such as those typically used as a dressing. In some examples, the lower and upper layers or strips are approximately 50 mm in length, and 5-25 mm in width. In at least some other examples, the lower layer is approximately 80 mm in length, and approximately 30 mm in width. In some examples, the lower and upper layers have the same width as the insert or are slightly wider than the insert. In some examples, the lower and/or upper layers are substantially longer than they are wide (e.g., 2×, 3×, 4×, 5× or 6× longer than they are wide). This length to width ratio may provide adequate surface area of adhesion over which to spread the tension. A longer upper and/or lower material may also reduce and/or eliminate the tilting effect of the insert's upper step falling over to contact the lower layer of material.

The upper and lower layers 106,108 may be formed of the same or similar material, size and/or configuration. Alternatively, the upper and lower layer may share some characteristics or may be formed of a different material, size and/or configuration.

Lower layer 106 may be formed of a woven, or non-woven material. One example of a suitable material is STERI-STRIP® reinforced adhesive skin closures. In some examples, the lower layer includes a suitable non-woven material that prevents the absorption of blood and/or fluids, such as a polyurethane material. In some examples, lower layer 106 may have an adhesive lower surface that will be in contact with the skin. Alternatively, both surfaces of the lower layer 106 may have an adhesive. The material of lower layer 106 may be isotropic (i.e., it has equal elasticity in any direction along its plane). Alternatively, the material of lower layer 106 may be anisotropic (i.e., it has variable elasticity in at least two directions along its plane). For example, the lower layer 106 may have a first elasticity along its longitudinal axis, and a second elasticity perpendicular to its longitudinal axis, the first elasticity being greater than the second elasticity, or vice versa.

In some examples, lower layer 106 may be reinforced with longitudinally-oriented polymer filaments or fiberglass strands (e.g., filaments 130 in FIG. 2) that results in anisotropic characteristics so that the material does not stretch along its longitudinal axis, but does stretch in lateral directions. FIG. 2 shows one example of a hemi-bridge having an insert 105 disposed on a lower layer 106, the lower layer having longitudinally-oriented filaments 130. For the sake of simplicity, the upper layer is not shown. As shown in FIG. 2, the filaments may be located along only a portion of the length of the lower layer. Thus, filaments 130 may extend along the entire length of the lower layer, more than half of the length of the lower layer, half of the lower layer, or less than half of the length of the lower layer (e.g., the filaments may extend along 100%, 90%, 80%, 70%, 60%, 50%, 40%, 30%, 20% or less of the length of the lower layer). Alternatively, lower layer 106 may include no filaments at all. That is, lower layer may be isotropic, or may be anisotropic without the use of filaments through the use of other techniques. The lower layer may be isotropic at one end, and anisotropic at another end (e.g., it may include filaments at the proximal end where the insert is disposed, and no filaments on the opposite end). In some example, the lower layer may be selected to prevent or reduce the possibility of skin maceration.

Upper layer 108 may be formed of a woven, or non-woven material. In some examples, the upper layer includes a suitable non-woven material that prevents the absorption of blood and/or fluids. In some examples, upper layer 108 may have an adhesive lower surface that will be in contact with the insert or the lower layer. The material of upper layer 108 may be isotropic (i.e., it has equal elasticity in any direction along its plane). Alternatively, the material of upper layer 108 may be anisotropic (i.e., it has no stretch in at least one direction along its plane).

In some example, upper layer 108 may also be reinforced with longitudinally-oriented polymer filaments or fiberglass strands that results in anisotropic characteristics so that the material does no stretch along its longitudinal axis, but does stretch in lateral directions. Filaments 130 may extend along the entire length of the upper layer, more than half of the length of the upper layer, half of the upper layer, or less than half of the length of the upper layer (e.g., 100%, 90%, 80%, 70%, 60%, 50%, 40%, 30%, 20% or less). Alternatively, upper layer 108 may include no filaments at all. That is, upper layer may be isotropic, or may be anisotropic without the use of filaments. The upper layer may be isotropic at one end, and anisotropic at another end (e.g., it may include filaments at the proximal end where the insert is disposed making it inelastic or less elastic in a longitudinal direction, and no filaments on the opposite end making it more elastic in the longitudinal direction).

By choosing the appropriate elasticity for the upper and/or lower layers (e.g., isotropic vs. anisotropic), an impedance mismatch between the skin and the lower layer of material may be lowered, reducing the possibility of blister formation. Blister formation may result from non-yielding materials adherent to the skin as tension imparted to the skin creates shearing forces in the horizontal plane of the skin that separate layers of the skin from one another (e.g., separating the epidermis from the dermis). In some examples, the presence of anisotropic segments that can mimic the elasticity of the underlying skin at predefined locations within the upper and/or lower layer may alleviate the shearing forces at certain positions. In some examples, the presence of isotropic segments at predefined locations within the upper and/or lower layer may alleviate the shearing forces at certain positions. Additionally, filaments in the upper and/or lower layers may serve to stabilize the insert to keep it upright, and prevent it from tipping.

As previously noted, upper and lower layers may share some or all of the characteristics. For examples, the two layers may be formed of the same material, may have the same non-woven construction, may include the same type of adhesive, may have the same elasticity profile, and/or the same extent, direction, amount and/or orientation of filaments.

Figure 3:
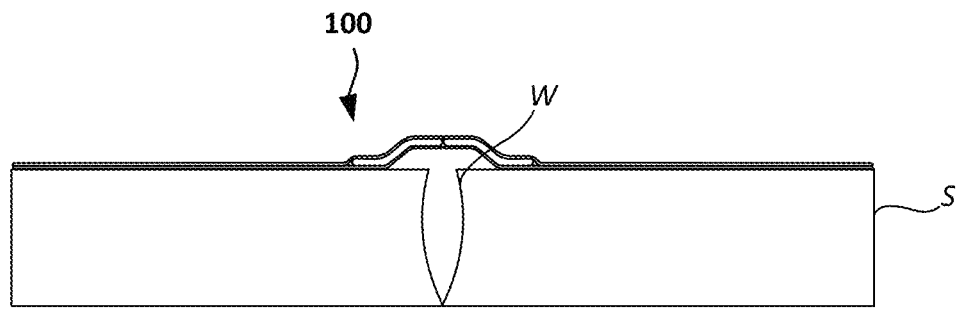
FIG. 3 is a schematic cross-sectional view showing a pair of hemi-bridges being used to close a wound.

In use, a hemi-bridge 100 may be laid flat on the skin surface on both sides of the wound, the lower layer of material contacting the skin surface. The edge of the hemi-bridge 100 may be disposed at the edge of the wound, or may be set back from the wound by 2 to 5 mm. Preferably, an adhesive on the lower surface of the lower layer couples the lower layer to the skin. The stair-shaped insert 105 is disposed above the lower layer and covered by the upper layer. In at least some examples, two hemi-bridges 100 are used, the two bridges facing one another and being disposed on either side of a wound "W" (FIG. 3). A suture pattern may be used to gather the ends of the wound with the hemi-bridges. Details of the various patterns will be described below. However, generally, the hemi-bridges may be brought together such that the upper steps of the two hemi-bridges come in contact with one another when gathered by the sutures. Alternatively, only a single pair of hemi-bridges may be used. Multiple pairs of hemi-bridges (e.g., 4 hemi-bridges) may also be used in some examples.

Figure 4A:
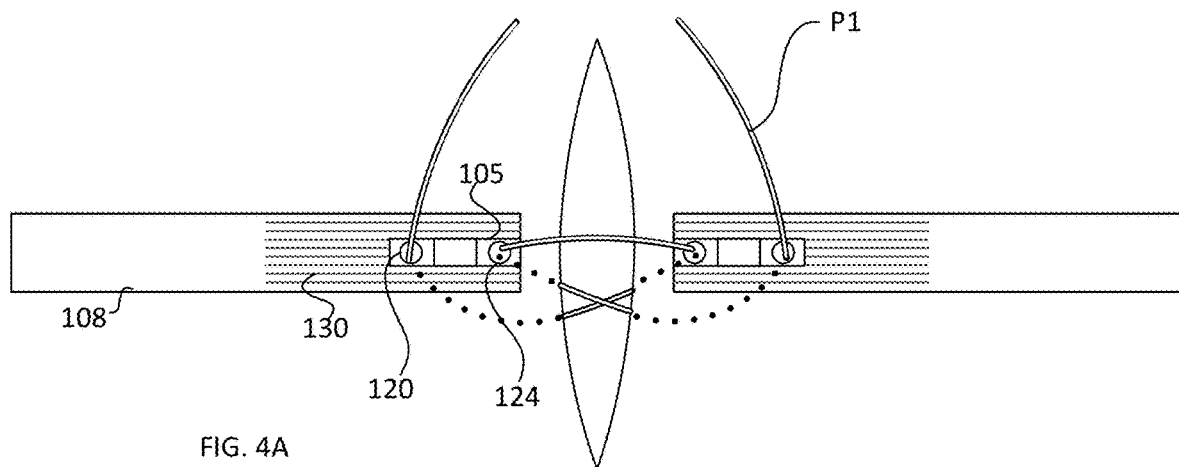
Figure 4B:
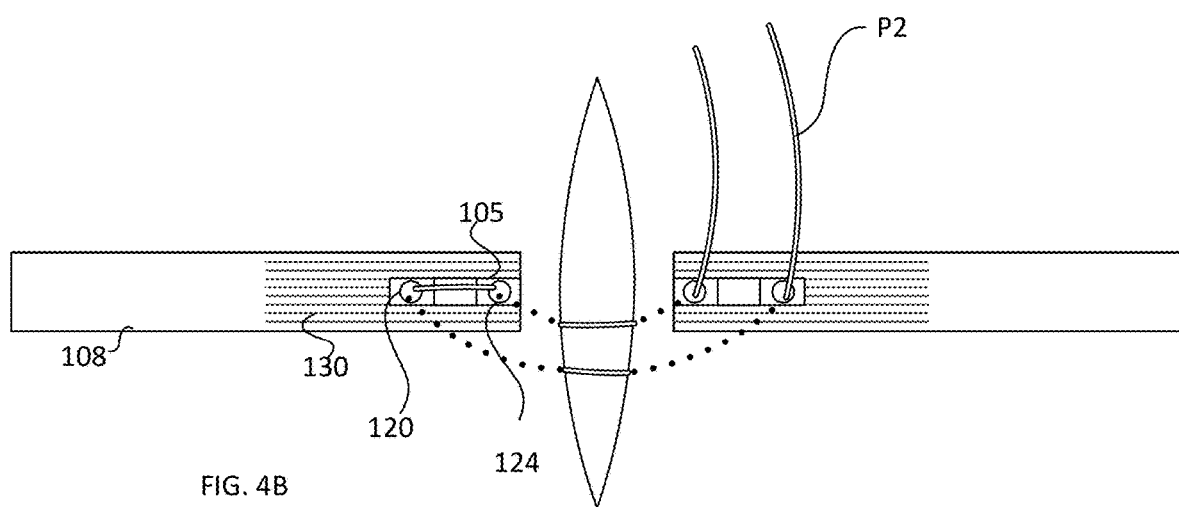
Figure 4C:
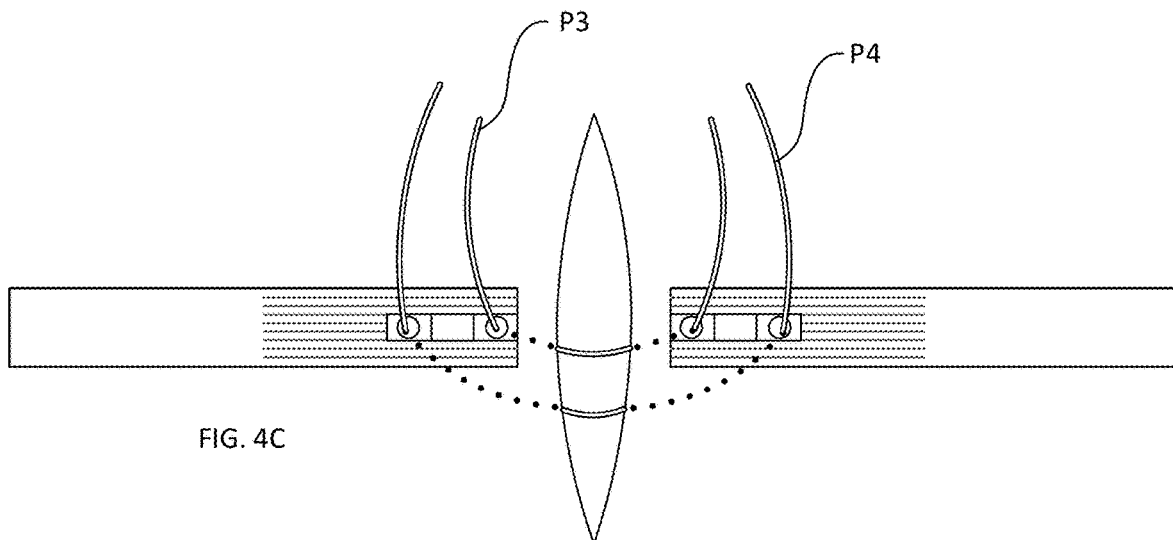
Figure 4D:
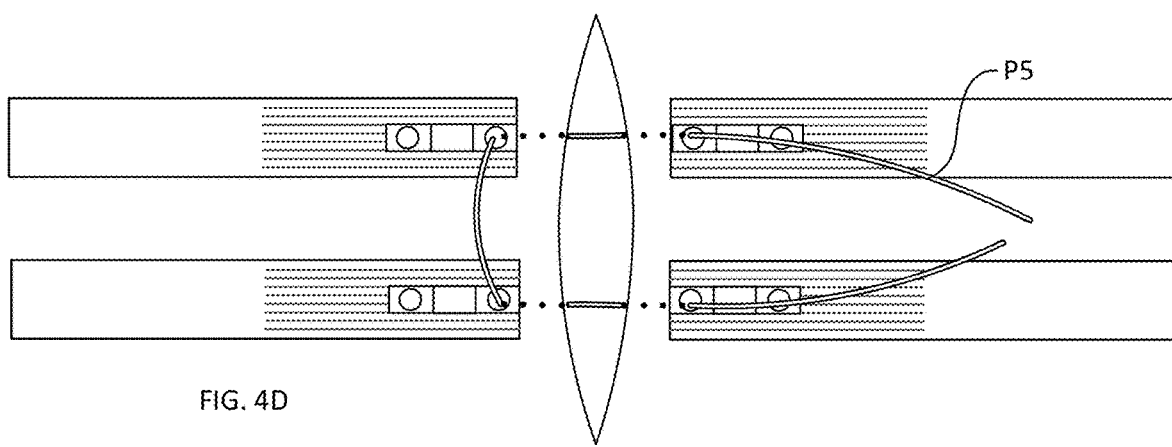
Figure 4E:
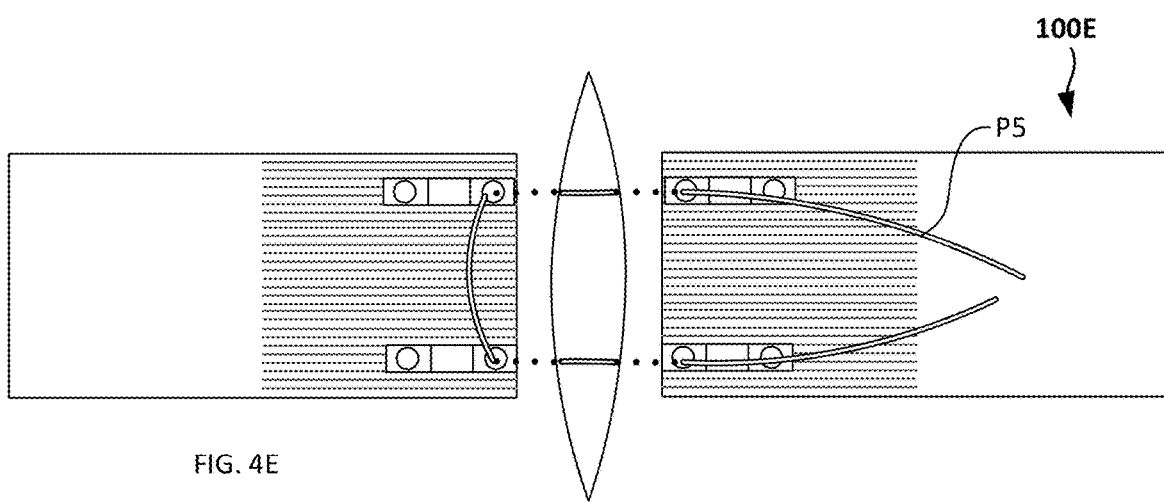

FIGS. 4A-C illustrate various suture patterns P1-P5 being used to gather ends of a wound using exemplary hemi-bridges. In FIG. 4A, a far-near-near-far pulley suture pattern P1 is formed with the suture. In this case, far refers to passing through an eyelet 120 on the lower step, while near refers to passing through an eyelet 124 on the upper step, and the "far-near-near-far" refers to the sequence in which the suture passes through these eyelets. In this and other examples, a dotted line indicates that the suture is under the skin and/or hemi-bridge and cannot be seen from a top view. In FIG. 4B, a far-far-near-near vertical mattress suture pattern P2 is shown. In FIG. 4C, two possible suture patterns P3,P4 are shown, the first being a simple interrupted near-near suture pattern P3, and the second being a simple interrupted far-far suture pattern P4. Finally, in FIGS. 4D-E, horizontal mattress suture patterns P5 are shown. In FIG. 4D, two hemi-bridges are disposed on either side of the wound, for a total of four hemi-bridges, each hemi-bridge being vertically aligned with another hemi-bridge adjacent to it, and horizontally aligned with an opposing hemi-bridge opposite the wound. Instead of using multiple hemi-bridges on either side of the wound, a compound hemi-bridge may be formed as shown in FIG. 4E, the compound hemi-bridge having widened upper and lower layers of material, and two or more inserts sandwiched between the layers (e.g., two, three, four, five or more inserts) and aligned with one another. Optional filaments are shown in this configuration, the filaments being located on one or two sides of the either the upper layer, the lower layer, or both.

Using any of the suture patterns described above, or other suitable one, a physician may apply tension to the suture of up to 10 or 20 Newtons, or between 5 and 30 Newtons, to gather the two ends of the wound together. The hemi-bridges, and specifically the inserts, may act to elevate the suture above the wound, and may allow the physician to apply more force than possible without the use of the hemi-bridges. Moreover, the use of device having a rigid insert as described may prevent cheesewiring of a suture closing a wound under tension. For example, a wound closed under 20 Newtons of force without the present devices would likely suffer from cheesewiring of the suture through the skin. However, by using any of the present devices and techniques, the force of the suture may be substantially borne by the insert, and then transmitted to the entire area of the device, the relatively large surface area of the device being helpful in prevent injury or damage to the patient's skin. Additionally, elevation of the suture may reduce the likelihood of "track marks" on the patient's skin.

In some examples, the shape of the insert may be different. For example, FIG. 5A shows a hemi-bridge structure 500a having a proximal end 502 and a distal end 504, a wedge-shaped insert 505a having a step and upper and lower layers of materials 506,508 sandwiching the insert. FIG. 5B shows a hemi-bridge structure 500b having a proximal end 502 and a distal end 504, a ramp-shaped insert 505b and upper and lower layers of materials 506,508 sandwiching the insert. Any of the inserts in FIGS. 1-6 may be used to elevated the suture above the wound surface.

Figure 4F:
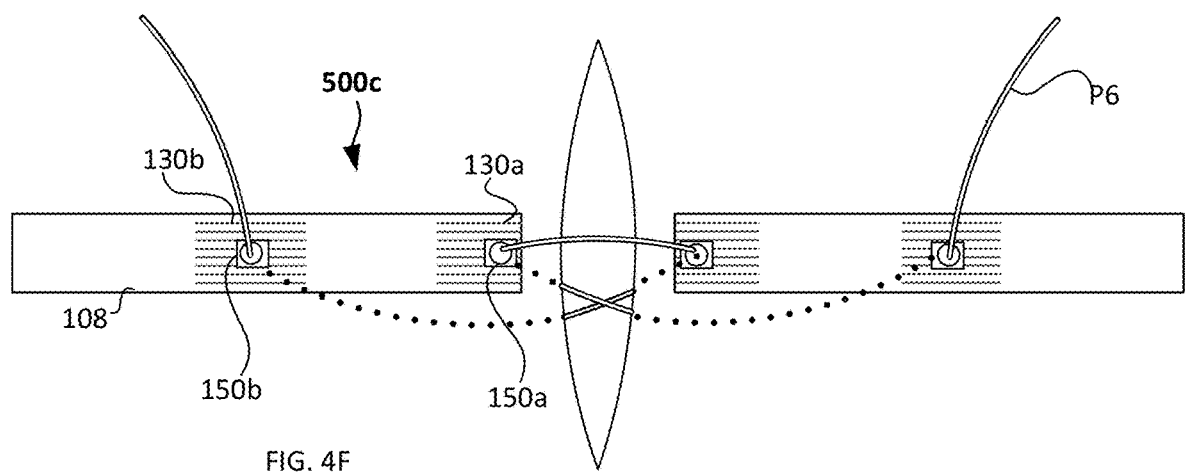

FIG. 5C shows another example in which two separate steps are formed instead of a continuous hemi-bridge. Specifically, bridge 500c includes a first step 150a and a second step 150b, the height of the first step being greater than the height of the second step. Alternatively, the first and second steps 150a,150b may be of a same height. Each step may include an eyelet as described above. The two steps are not directly connected to another, but are both sandwiched by upper and lower layers of material. In at least some examples, the upper and/or the lower layer of material includes sets of filaments 130a,130b disposed adjacent each of the steps, but the spacing between the two steps does not include such materials. One example of this embodiment in use is shown in FIG. 4F, in which bridge 500c is being used in a pulley suture arrangement P6.

Additionally, the top step of the insert may have interdigitation including a series of spaced projections 606 and depressions 607 so that two opposing hemi-bridges 605a, 605b may mate together with the projections and valleys of the two hemi-bridges interlocking with one another when the two components come together (FIG. 6). FIG. 7 illustrates another example of interdigitation where the hemi-bridges 705a,705b include a high-low tooth configuration arranged to mate with one another and form a complete bridge.

To manufacture the hemi-bridges, a rigid or substantially rigid insert such as those described above (e.g., a thermoplastic insert) may be sandwiched between upper and lower layers in a large sheet. The components may be die cut to the appropriate size, and holes may be formed in the insert to create eyelets. The assembly may be placed in a heated press, the press having a temperature that exceeds the melting temperature of the insert, but be below the safe temperature of the upper and lower layers. The heated press may also include an elevated portion to create the step in the insert. In addition to forming the step in the insert, the heated press may also reduce the presence of sharp edges at the bottom of the hemi-bridge by curling the sides of the device upward to redirect lower edges away from the skin of the patient. After proper heating, the assembly may be removed and cooled. The finished device may then be used to close a wound as described above. Alternatively, the insert may be formed separately (via injection molding, 3D printing or other techniques) and later coupled to the upper and lower layers.

The suture securing devices, systems, and methods described herein may be used to secure a suture and reduce or eliminate the likelihood that a suture may become inflamed, infected, ingrown, and/or reopened and increase the length of time that the suture can remain in place, among other purposes. Additionally, the devices disclosed herein may be capable of allowing a physician to apply a large force when tying a suture without damaging nearby tissue, and in some cases may be used to avoid the usage of skin grafts to close relatively large wounds.

FIG. 8 is schematic cross-sectional view of a hemi-bridge 800 according to yet another embodiment. Hemi-bridge 800 generally extends between a proximal end 802 and a distal end 804, the proximal end being relatively closer to the wound, and the distal end being relatively farther from the wound. Hemi-bridge may include an insert 805 sandwiched between two layers of material. Specifically, the two layers of material include a lower layer 806, and an upper layer 808. Lower and upper layers 806,808 may be coupled together via an adhesive where they are in contact. Additionally, insert 805 may be coupled via adhesive, or other suitable means, to the top of the lower layer 806 and/or the bottom of the upper layer 808.

Insert 805 may be formed of any of the materials discussed above with reference to insert 105, such as various thermoplastics and/or metals, and lower and upper layers 806,808 may be formed of the same materials as lower and upper layers 106,808. As shown, insert 805 may be stair-shaped and includes a lower step, an inclined ramp and an upper step similar to the configuration of FIG. 1. As best shown in FIG. 9, each of the upper and lower steps may include a respective eyelet 820,824 for receiving a suture. In at least some examples, the eyelets are circular and of a same size as shown, or may be in any of the configurations previously described.

Hemi-bridge 800 may be divided into three zones, z1,z2, z3. First zone z1 may include insert 805 sandwiched between lower and upper layers 806,808. Second zone z2 may include only the lower and upper layers 806,808 without the insert 805. Third zone z3 may include only a single material, such as lower layer 806. The three zones z1-z3 may form differential stiffness zones that become less stiff further from the wound edge (e.g., greatest stiffness at proximal end 802 and smallest stiffness at distal end 804). First zone z1 provides the greatest stiffness, primarily due to the presence of the essentially inelastic insert 805. Second zone z2 may be less stiff with its bi-layer of non-woven material (e.g., lower layer 806 and upper layer 808), which may be fused with an adhesive or coupled together in any suitable manner. Third zone z3 may be the least stiff with a monolayer of non-woven material (e.g., only lower layer 806 or only upper layer 808) and may serve as the most reliable adhesive zone.

Without being bound by any particular theory, it is believed that in the vicinity of the wound (i.e., closer to first zone z1) will be exposed to more fluid. All dressings have a tendency to lose adhesion with a certain distance of the edge of the dressing. For example, a 10 mm dressing may have 1-2 mm of loss of edge adhesion due to moisture, etc. Thus, after a few days, a 10 mm wide strip may really only have 6-8 mm of useful adhesion with further deterioration thereafter. Thus, having a wider and longer third zone, z3, may provide much more width prior to losing adhesion and will also tend to reduce shear through higher cross-sectional surface area.

In some examples, insert 805 may be formed as a flat piece that is bent to include a step as previously discussed. In at least some examples, the step forms an angle θ of between 20 and 60 degrees. In at least some examples, the angle θ is between 30 and 50 degrees. In at least some examples, the angle θ is equal to or approximately 40 degrees as shown in FIG. 10.

As shown in the perspective views, the lower and upper layers 806,808 and the insert 805 may have a shape and a size that matches other components adjacent thereto. For example, both the lower and upper layers 806,808 may have a generally rectangular stepped-shape that matches the insert 805 at first zone z1. Both lower and upper layers 806,808 may have a narrowed neck at second zone z2, and lower layer 806 may have a wider and longer rectangular shape at third zone z3.

In at least some examples, the hemi-bridge has a total length of approximately 2 to 3 cm, or about 2.3 to 2.4 cm. Third zone z3 may have a length that is 40% to 50% of the total length of the hemi-bridge. First and second zones z1,z2 may be approximately equal in length, or first zone z1 may be slightly longer than second zone z2. Third zone z3 may be the widest of the three zones, and may have a width of between 0.5 and 0.6 cm. Second zone z2 may be the narrowest and may have a width of between 0.3 and 0.35 cm. First zone z1 may be wider than second zone z2 and narrower than third zone z3 and may have a width of between 0.4 and 0.5 cm. The surface area may be greatest in third zone z3 and smallest in second zone z2. Insert 805 may have a thickness of between 0.010 cm and 0.030 cm and specifically about 0.020 cm.

In at least some examples, two hemi-bridges 800 are used, the two bridges facing one another and being disposed on either side of a wound "W" (FIG. 12). A suture pattern may be used to gather the ends of the wound with the hemi-bridges using any of the suturing techniques and patterns described above with reference to the other embodiments. However, generally, the hemi-bridges may be brought together such that the upper steps of the two hemi-bridges approach each other, or come in contact with one another when gathered by the sutures.

Although the hemi-bridges have been disclosed as having an insert including an upper step, a lower step and a connecting ramp, other variations are possible. For example, instead of having an inclination angle as previously described, the insert may be completely flat. For example, hemi-bridge 900 extends between ends 902,904 and includes a planar insert 905 that is covered by lower layer 906 and upper layer 908 (FIGS. 13A-B). It will be understood that in manufacturing the device, upper and lower layers of material may sandwich an insert and form a configuration similar to the flat configuration of FIGS. 13A-B. The flat sandwich of lower layer-insert-upper layer may be collectively die cut before thermoforming at a high temperature (e.g., 200 degrees F.) to form an inclined angle and any number of steps. It will be understood that the flat configuration may be used in certain applications, and that other applications may require thermoforming to provide an angle of 10, 20, 30, 40, 50 or 60 degrees. Thus, the angle of inclination may be formed as desired for a specific application.

Even without an inclination, the flat configuration of hemi-bridge 900 may elevate a suture or other fastening element via insert 905 to achieve one or more of the advantages described above. In at least some examples, the lower layer 906 is formed of a non-woven polyester with an adhesive backing, insert 905 is formed of PETG, and upper layer 908 is formed of polyethylene. In at least some examples, the lower layer 906 may also partially or entirely include an elastic tape having variable thickness such as Microfoam tape made by 3M®, the tape being capable of having variable elasticity due to the variable thickness. The non-woven polyester lower layer 906 may have the PETG insert adhered to its top surface at one end, the inert having one or more (e.g., two) eyelets. Due to the layering of material, a stepped configuration having three zones, z1,z2, z3 is formed, first zone z1 having all three layers, second zone z2 having two layers, and third zone z3 having only the lower layer.

As shown in FIG. 13B, third zone z3 may be the widest portion of the device 900 with only a single layer of stretchable and absorbent adhesive material. The material of lower layer may experience a high amount of strain under force, so an elastic material may be used to allow less shear force on the trailing edge, a common problem in adhesive dressings. Second zone z2 may be a narrowed central portion of two layers. In addition to the lower layer, the second zone may have a polyethylene upper layer 908 to resist blood and fluid from being absorbed into the dressing. The polyethylene layer may also provide strength and reinforcement for the narrow central zone. First zone z1 may be the strongest and most rigid due to the presence of the insert 905. Insert 905 may resist tearing under high tension (e.g., up to 20 N or 30 N of force) and may also elevate the suture material above the skin.

First and second zones z1,z2 may allow blood to be wiped off the device and provide a stiff connection to third zone z3, where shear forces are reduced by the single layer of lower stiffness material. Thus, different regions may be formed with increasing elasticity from first zone z1 closer to the wound toward third zone z3 farthest from the wound. That is, first zone z1 may have the lowest elasticity, second zone z2 may have an intermediate elasticity, and third zone z3 may have the greatest elasticity. Conversely, first zone z1 may have the greatest stiffness, second zone z2 may have an intermediate stiffness that is less than the stiffness of first zone z1, and third zone z3 may have the lowest stiffness compared to the other three zones. The device 900 also increases in height as it gets closer to the wound to provide elevation.

Without being bound by any particular theory, it is the believed that the suture acts to not only apply tension to gather the wound, but also applies a downward force on the rigid insert. This downward force is helpful to keep a consistent contact of the adhesive of the lower layer with the skin. Additionally, a planar rigid insert may evenly distribute this pressure on the skin, and the downward force may reduce the likelihood of maceration.

Figure 13C:
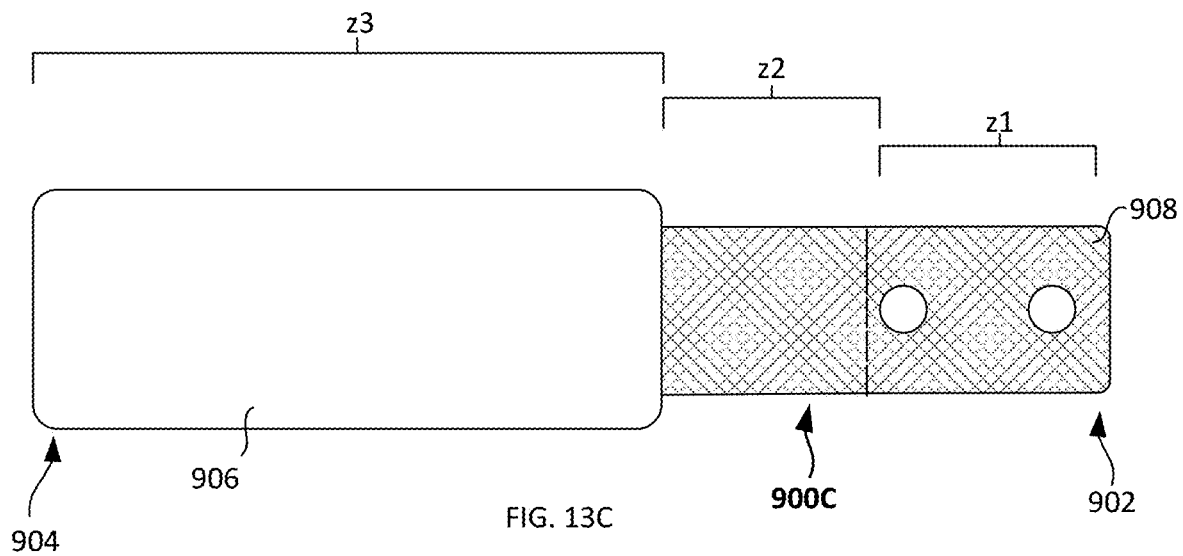

FIGS. 13C-F are schematic top and side views showings several variations of the flat hemi-bridge of FIGS. 13A-B. In FIG. 13C, a hemi-bridge device 900C is formed that is similar to that of FIGS. 13A-B, but excludes the tailored or narrowed neck in second zone z2. Instead, the lower and upper layers present a continuous width that is present in first and second zones z1,z2 as shown, while third zone z3 is wider than both.

Figure 13D:
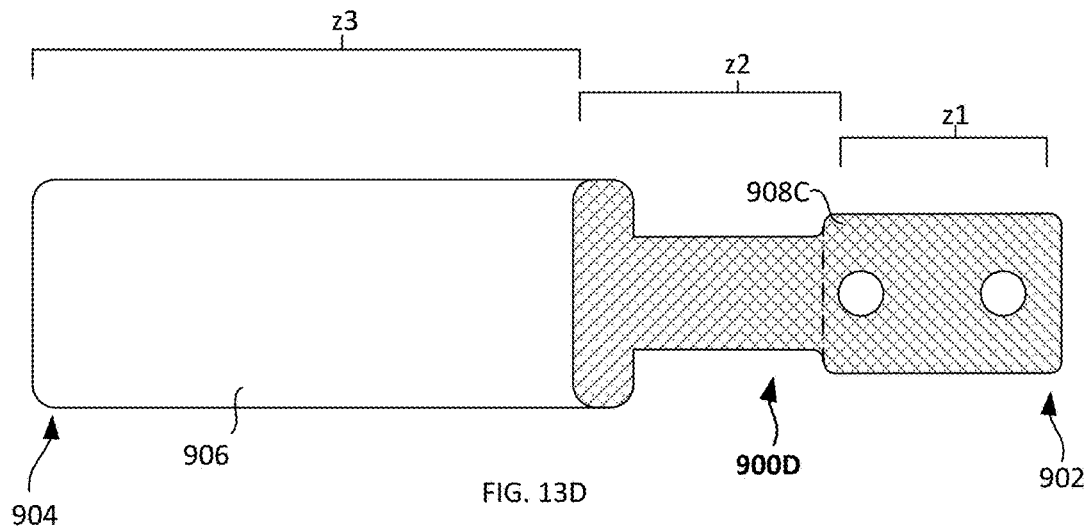

In FIG. 13D, a hemi-bridge 900D includes the narrowed neck formed in second zone z2, but the upper layer 908C partially extends over the wider portion of lower layer 906 as shown so that second zone z2 having two layers of material is slightly longer than the embodiment of FIGS. 13A-B. In this example, upper layer 908C may have three widths including a first width adjacent the insert, a second width at the tailored neck and a third width at the wider region of the lower layer. It will be understood that the embodiments of FIGS. 13C and 13D may be combined so that the upper layer only includes a constant first width adjacent the insert and a majority of the second zone z2, and a second width overlying the wider region of the lower layer.

Figure 13E:
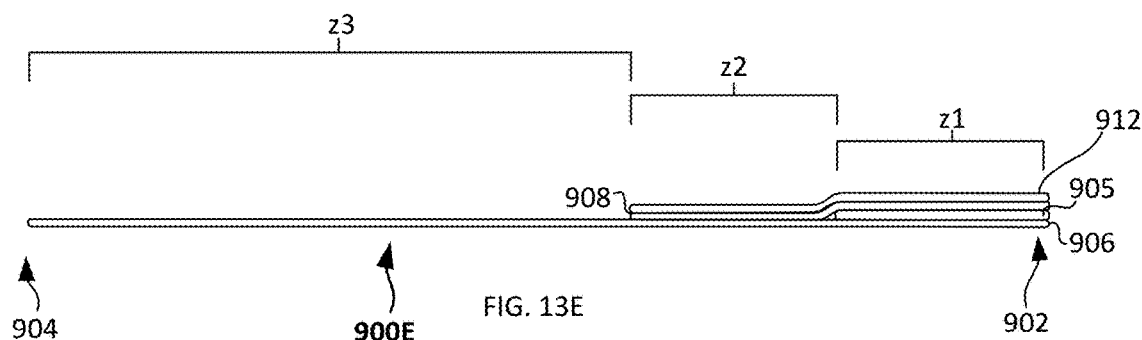

FIG. 13E illustrates yet another embodiment of a hemi-bridge 900E, the hemi-bridge having a lower layer 906, an insert 905 and an upper layer 908 as described above. Hemi-bridge 900E further includes a covering layer 912, formed of a waterproof material, the covering layer 912 being disposed on and partially or fully extending over the upper layer 908. Covering layer 912 may be of the same length as upper layer 908 and may be disposed in first zone z1, and extend into second zone z2 to provide additional stiffness to second zone z2.

Figure 13F:
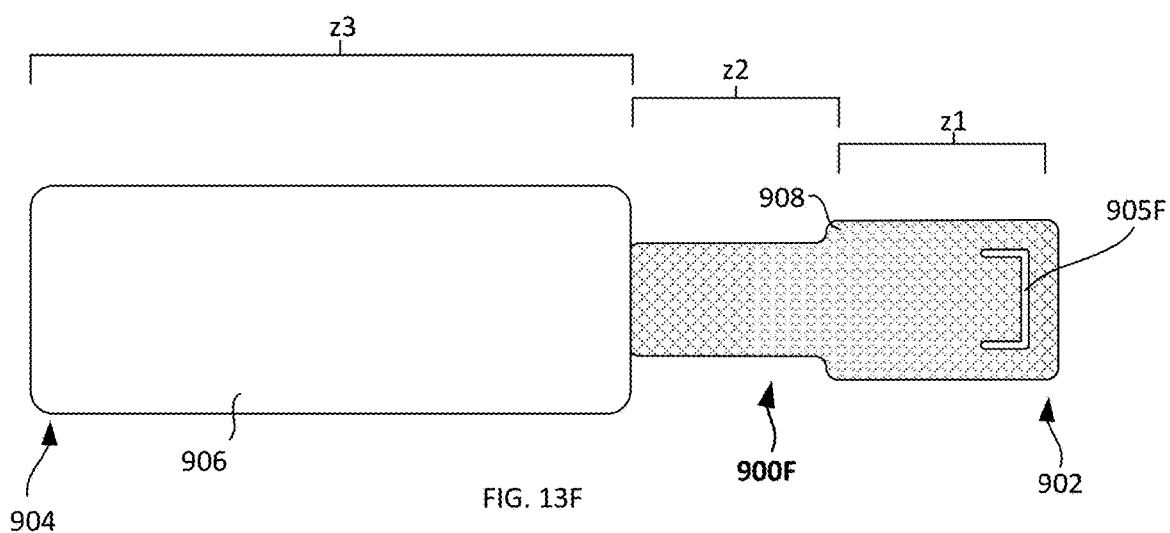

In FIG. 13F, yet another embodiment is shown, which is similar to that of FIG. 13B, except that hemi-bridge 900F includes a rigid member 905F embedded and/or affixed between the lower and upper layers, the rigid member being configured and arranged so that the user can pass a suture over or around it. In some examples, the rigid member is staple-shaped as shown, or curvilinear. Rigid member 905F may be formed of any of the materials described herein for the inserts such as, for example, thermoplastics or metals. It will be understood that this feature may be combined with any of the embodiments described herein, and that the rigid members may be substituted for the inserts described in any of the disclosed embodiments.

In use, two hemi-bridge devices 900 may be laid flat on the skin surface on either side of the wound, the lower layer of the device contacting and being adhered the skin surface (FIG. 14A). The edge of the hemi-bridge 900 may be disposed at the edge of the wound W14, or may be set back from the wound W14 by 2 to 5 mm. A suture S14 may enter a first eyelet of the first hemi-bridge, pierce the skin and traverse the wound through the underlying tissue, exiting the first eyelet of the second hemi-bridge as shown in FIG. 14A. Suture S14 may be used to gather the margins of the wound and a knot may be tied (FIG. 14B). Generally, the hemi-bridge devices are disposed near the middle of the wound as shown, although different configurations are possible. With the center of the wound gathered (FIG. 14B), additional sutures S14' may be used to gather edges of the wound and completely close the wound (FIG. 14C).

FIG. 14D is an illustration of a finite element analysis showing stress profiles of a wound closed with a hemi-bridge device (left image), and a wound closed without a hemi-bridge device (right image). In a wound closed with only sutures, stress is concentrated near the wound edge. The stress is greatest at the wound edge and decreases radially outward from the wound edge. As shown, the use of a hemi-bridge device allows for stress to be dispersed over a larger area away from the wound in a profile that mimics the perimeter of the device. Specifically, the hemi-bridge device substantially reduces or practically eliminates stress at the wound edge with the greatest stress being experienced near the eyelet of the device. A substantial portion of the total is stress is distributed over the area of the hemi-bridge device.

It will be understood that other ways of using the hemi-bridge devices are possible. For example, as shown in FIGS. 15A-C, surgical staples S15 or clips may be used instead of sutures to close wound W15 and may extend through any of the eyelets of the insert. Additionally, combinations of various kinds of fastening elements (e.g., sutures, clips, staples, etc.) may be used, and the eyelets of the device may be configured to accept any or all kinds of fastening elements.

In another example (FIG. 16A-B), hemi-bridge devices may be used to close larger wounds W16. In this example, wound W16 may have missing underlying tissue such that piercing and traversing the underlying tissue is difficult or impossible. In such a case, a suspended suture S16 may be used to gather tissue without traversing the underlying tissue. In one example, skin may be missing below zone z1 of the device, but may be present in zones z2 and z3. In such a situation, a suture may not pierce the skin adjacent first zone z1, but the hemi-bridge device may remain secured to the skin via zones z2 and z3 only.

Figure 17A:
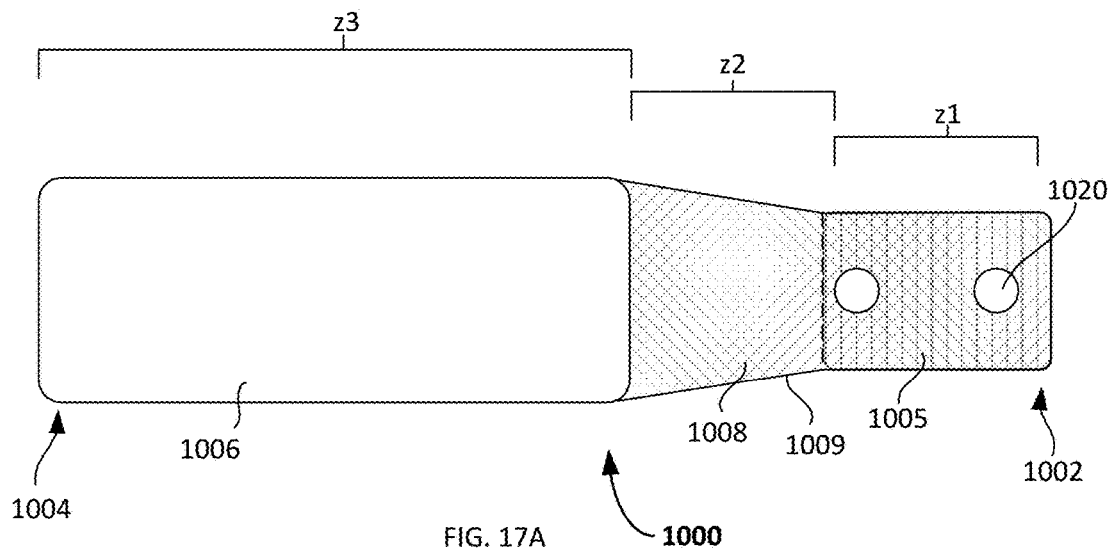
Figure 17B:
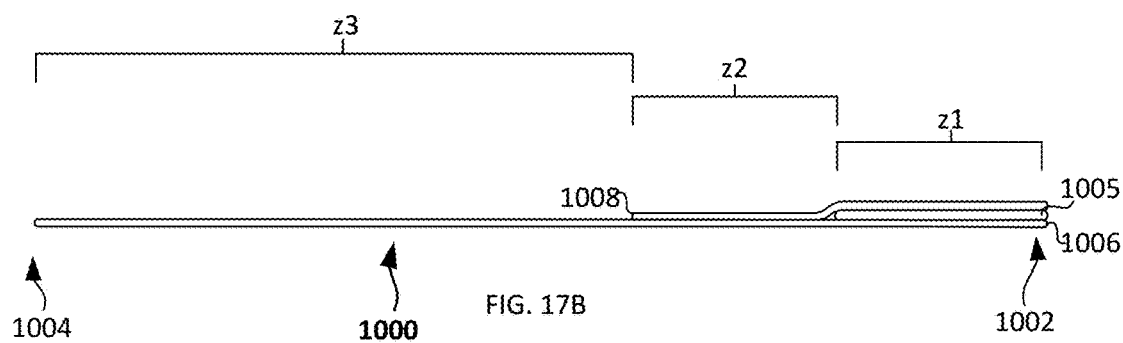

FIG. 17A is a schematic top view of another embodiment of a hemi-bridge, and FIG. 17B is a side view of same. Generally, hemi-bridge 1000 extends between proximal and distal ends 1002,1004 and includes a planar insert 1005 disposed between lower layer 1006 and upper layer 1008. It will be understood that in manufacturing the device, upper and lower layers of material may sandwich the insert and form a configuration similar to the flat configuration of FIGS. 13A-B. It will be understood that the flat configuration may be used in certain applications, and that other applications may require thermoforming to provide an angle of 10, 20, 30, 40, 50 or 60 degrees as previously described. Thus, the angle of inclination may be formed as desired for a specific application.

Each of the lower layer, the upper layer and the insert may be formed of any of the materials described above. For example, the upper and/or lower layers may be formed of any one of polyethylene, polyurethane, nylon, natural and/or synthetic materials, fabrics, cotton or suitable combinations thereof. In at least some examples, the upper and/or lower layer may be formed of a transparent material so that the wound may be inspected without removing the device. Due to the layering of materials, a stepped configuration having three zones, z1,z2,z3 is formed, first zone z1 having all three layers, second zone z2 having two layers, and third zone z3 having only the lower layer.

Notably in FIG. 17A, second zone z2 includes a transitioning edge 1009 that gradually widens from the first zone z1 to the third zone z3. Specifically, second zone z2 may include both the lower layer 1006 and the upper layer 1008 so that the two layers extend along the transitioning edge 1009. In at least some other examples, insert 1005 also extends, partially or fully along, transitioning edge 1009.

Figure 17C:
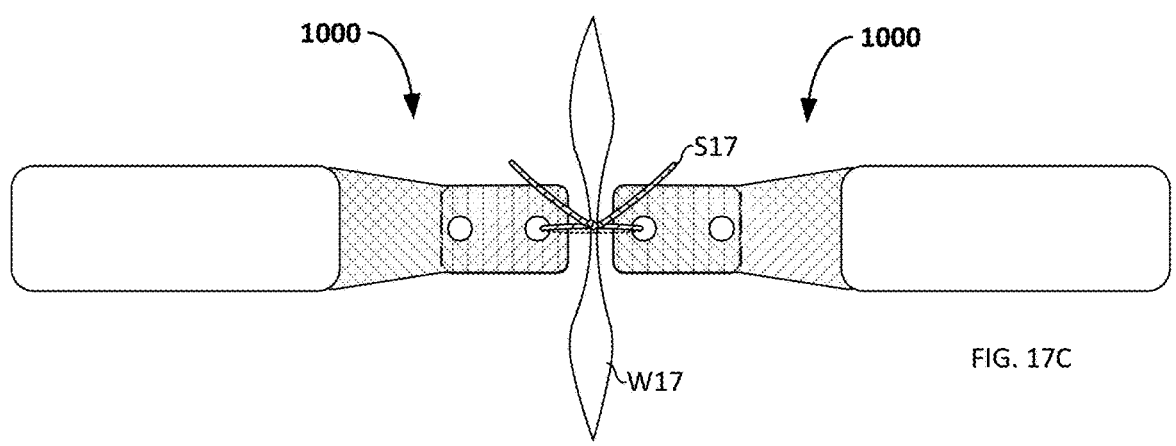

As shown in FIG. 17C, hemi-bridge devices 1000 may be used to close large wounds W17, similar to the devices previously described. In this example, wound W17 may have missing underlying tissue such that piercing and traversing the underlying tissue is difficult or impossible. In such a case, a suspended suture S17 may be used to gather tissue without traversing the underlying tissue through eyelets 1020. In one example, skin may be missing below zone z1 of the device, but may be present in zones z2 and z3. In such a situation, a suture may not pierce the skin adjacent first zone z1, but the hemi-bridge devices 1000 may remain secured to the skin via zones z2 and z3 only. The gradual widening (e.g., linear or non-linear increase of the width) along transitioning edge 1009 may reduce the risk of tearing in the second zone or failure of the device and may allow for elongation of the device under high tension.

Figure 17D:
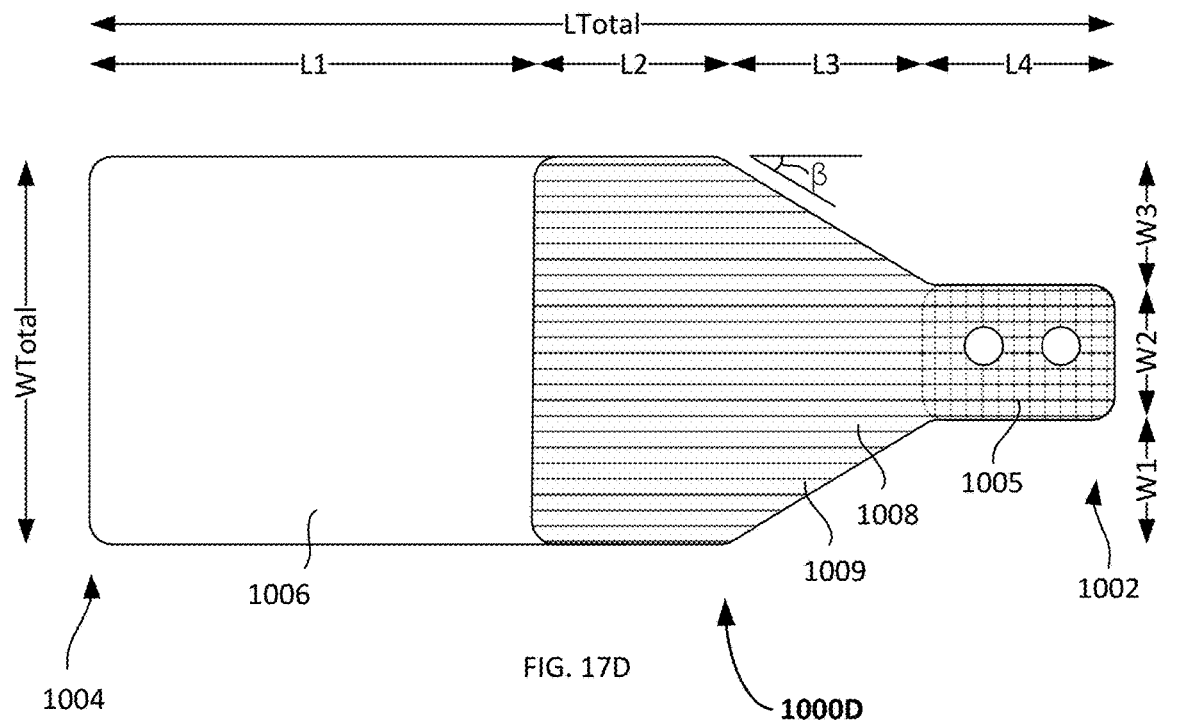
Figure 17E:
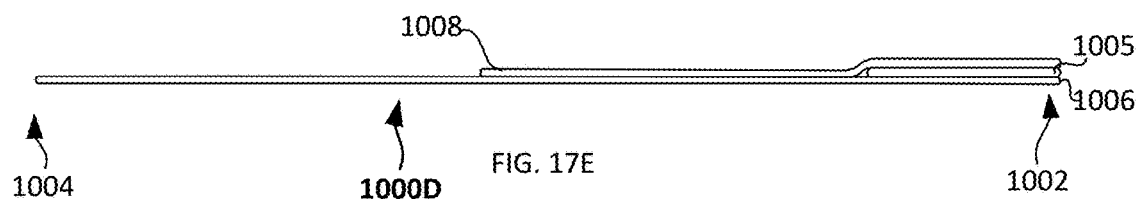

FIGS. 17D-E are schematic top and side views of another embodiment of a hemi-bridge. Hemi-bridge 1000D is similar to hemi-bridge 1000 of FIG. 17A, but has slightly different proportions. Generally, hemi-bridge 1000D includes a lower layer 1006, an upper layer 1008 and an insert 1005 disposed between lower layer 1006 and upper layer 1008. The proportions and dimensions of one possible hemi-bridge are provided herein, but it will be understood that the hemi-bridge may be scaled up or down as desired. For example, the hemi-bridge may be scaled down to ⅕, ¼, ⅓, ½, or ⅔ of the dimensions disclosed. Alternatively, the hemi-bridge may be scaled up to be 1.5×, 2×, 2.5×, 3× or 4× larger than the disclosed dimensions.

In the example shown, the total length, LTotal, of hemi-bridge 1000D may be approximately 80 mm, and the total width, WTotal may be about 30 mm. L1 may be about 35 mm, and each of L2, L3, L4 may be about 15 mm. The hemi-bridge may be symmetric about the longitudinal axis so that W1 and W3 are equal and about 10 mm each. In this example, W2 is also about 10 mm so that the insert is approximately 10 mm in width by 15 mm in length. The lower layer may be thicker than the upper layer or vice versa, and the insert may be thicker than either the upper or lower layers, or both layers combined. In some examples, the lower layer has a thickness between 1 mil and 20 mil and the upper layer has a thickness between 1 mil and 20 mil. The insert may have a thickness of between 5 mil and 100 mil. In this example, the transition angle β of the transitioning edge is approximately 30 degrees, although it will be understood that the transitioning edge may form a steeper or shallower angle as desired by varying the length L3. In at least some examples, the transition angle β is less than 45 degrees.

Figure 17F:
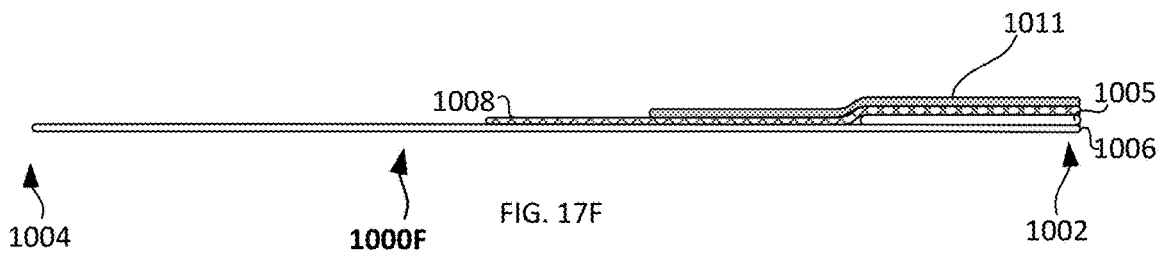
Figure 17G:
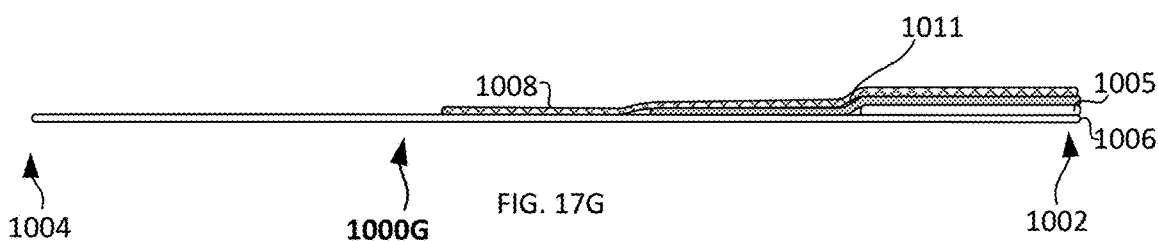

Optionally, a reinforcement 1011 may be disposed in certain sections (e.g., adjacent the transitioning edge) to prevent tearing of the hemi-bridge. As shown in FIG. 17F, hemi-bridge 1000F is shown that has a reinforcement layer 1011 disposed on top of upper layer 1008 and at least partially covering the upper layer 1008. Alternatively, reinforcement layer 1011 may be tucked beneath the upper layer 1008 as shown in FIG. 17G. In both cases, the reinforcement layer 1011 is shown as being shorter than the upper layer 1008, although it is understood that the upper layer and the reinforcement layer may be of a same length or coterminous. Reinforcement layer 1011 may be of a same material as the upper layer or the lower layer, or both. For example, in one embodiment all of upper layers 1008, lower layer 1006 and reinforcement layer 1011 may be formed of polyurethane.

FIGS. 18A-C are schematic side and top views of other embodiments of a hemi-bridge having waterproof coverings. As previously described, hemi-bridge 1100 extends between proximal and distal ends 1102,1104 and includes a planar insert 1105 that is covered by lower layer 1106 and upper layer 1108. It will be understood that in manufacturing the device, upper and lower layers of material may sandwich an insert and form a configuration similar to the flat configuration previously discussed. In these examples, additional upper and lower coverings 1112a,1112b formed of waterproof materials that envelope all surfaces and edges of the enclosed bridge assembly. FIG. 18B shows the covering 1112. It will be understood that the upper and lower coverings 1112a,1112b may be of the same shape and/or size, and may be conterminous with one another. As shown, the coverings 1112 may have a footprint that is slightly larger than all of the lower layer, upper layer, and insert so that an enclosing border 1113a is formed all around the assembly. This enclosing border may extend between 1/16 and 1/4 inches farther out from the assembly. Additionally, it will be understood that the upper and lower coverings 1112a,1112b may be coupled (e.g., joined, adhered, secured, ultrasonically welded, melted, etc.) together at the enclosing border to envelop the assembly. FIG. 18C illustrates an embodiment in which the hemi-bridge of FIG. 17A is enveloped with upper and lower coverings and a border 1113b is formed. Thus, any of the embodiments described herein may be fully covered or enveloped in this manner. Additionally, an adhesive may be disposed on the bottom of the device in second and/or third zones z2,z3 to allow the device to be coupleable to patient tissue. In at least some examples, instead of adding discrete waterproofing layers that create an envelope, a spray-on material may be applied to all or some surface of the bridge to waterproof it. This may include, for example, avocado oils, plant or animal-derived oils, beeswax, silicone, resins and suitable combinations thereof.

Figure 19A:
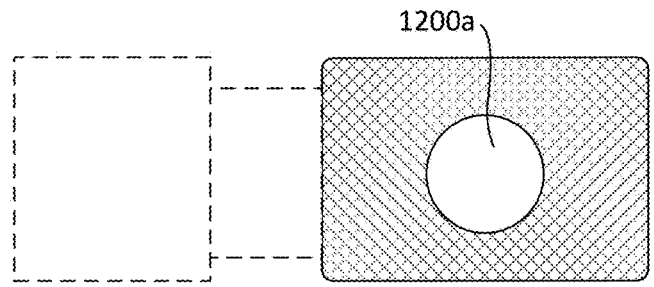
Figure 19B:
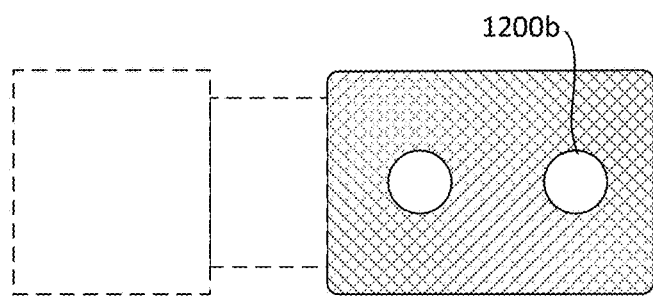
Figure 19C:
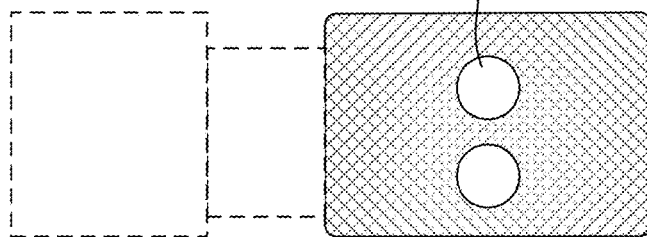
Figure 19D:
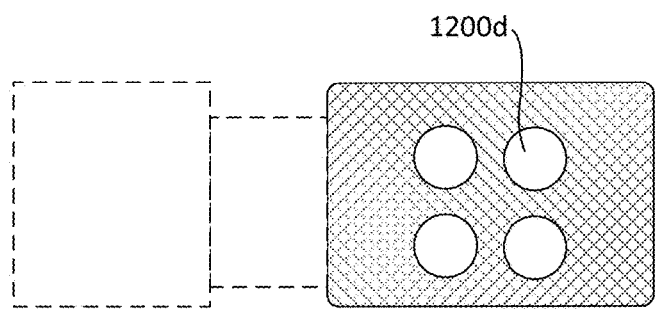

FIGS. 19A-D are schematic top views of several examples of eyelet arrangements on a hemi-bridge. Each of the eyelet arrangements described herein may be combined with any of the bridge configurations described in this disclosure. In FIG. 19A, a hemi-bridge 1200A includes an insert having a single eyelet 1220a centered vertically and horizontally within the insert. In FIG. 19B, a hemi-bridge 1200B includes an insert having eyelets 1220b arranged in a row of multiple eyelets (e.g., two, three or more eyelets) along the longitudinal axis of the device. In FIG. 19C, a hemi-bridge 1200C includes an insert having eyelets 1220c arranged in a column of multiple eyelets (e.g., two, three or more eyelets) arranged on a line perpendicular to the longitudinal axis of the device. In FIG. 19D, a hemi-bridge 1200D includes an insert having eyelets 1220d arranged in at least one row and at least one column of eyelets (e.g., two, three or more eyelets in each row and/or column).

FIG. 20A is a schematic top view of another embodiment of a hemi-bridge having a plurality of distinct digits. As shown, bridge 1300 may extend between proximal end 1302 and distal end 1304 and have three zones z1-z3 including an upper layer, a lower layer and one or more inserts as previously described. In this embodiment, bridge 1300 may include a plurality of digits 1310a,1310b,1310c (e.g., three digits) in first zone z1, each of the digits having an insert 1305 sandwiched between upper and lower layers 1308, 1306. Each of the digits 1310a-c may include one or more eyelets 1320 defined therein. In second zone z2, an upper layer and a lower layer may be coupled together. In third zone z3, only a lower layer 1306 is present. As shown, third zone z3 includes the lower layer being divided into a plurality of tabs 1330a-c. As shown, three parallel tabs 1330a,1330c are formed, each tab being aligned with one of the digits. In this example, the first and third tabs 1330a,c are of a same length, and second tab 1330b is longer than each of them. Alternatively, it will be understood that all three tabs 1330a-c may be formed of a same length. Without being bound by any particular theory, it is believed that by having distinct digits and/or tabs, movement of the patient's skin at one location will not translate to other locations and that the device may be better adhered and more securely close the wound.

FIG. 20B is a schematic top view of a hemi-bridge having a plurality of digits. As shown, bridge 1400 may extend between proximal end 1402 and distal end 1404 and have three zones z1-z3 including an upper layer, a lower layer and one or more inserts as previously described. Bridge 1400 is substantially similar to bridge 1300 except that it includes two tabs 1430a, 1430b instead of three tabs at the distal end. The two tabs 1430a,1430b are generally symmetrical about the central axis of the bridge, and include a cutout 1431 or concavity therebetween. In a third embodiment, shown in FIG. 20C, bridge 1500 has a number of digits 1510 adjacent proximal end 1502, but only a single curved tab 1530 adjacent distal end 1504.

Figure 20D:
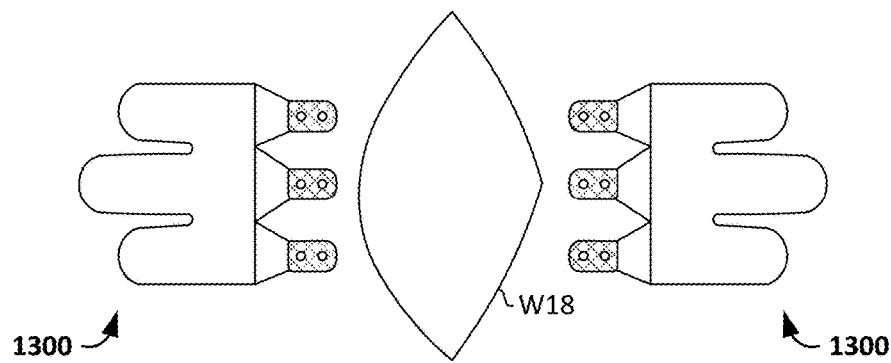
Figure 20E:
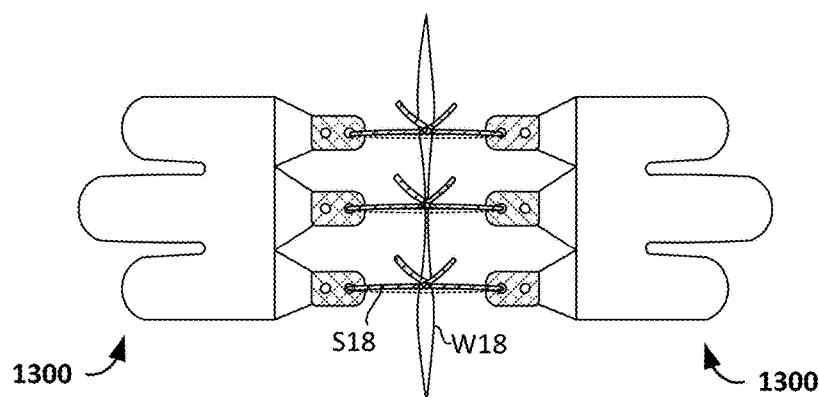
Figure 20F:
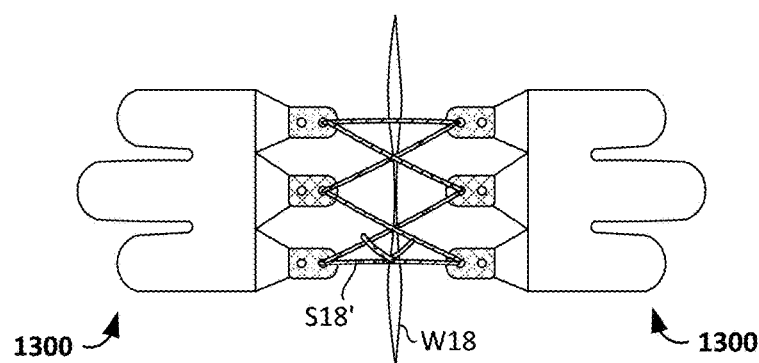

As shown in FIG. 20D-E, bridges 1300 may be used to close large wounds W18. In this case, two bridges 1300 are disposed on opposite sides of the wound with their digits facing and aligned with one another. A suture S18 including three loops may be used to gather tissue to close the wound (FIG. 20E). Other suture patterns are also possible. For example, a suture pattern S18' having a single continuous thread may be used as shown in FIG. 20F.

Instead of having two separate bridges disposed on either side of the wound, a unibody bridge 1600 may be formed having five zones z1-z5. FIGS. 21A-B illustrate one such embodiment in which a bridge 1600 extends between first end 1602 and second end 1604. Bridge 1600 may include a plurality of digits 1610 on each of the two ends at zones z1,z5, each of the digits having the three layers previously described (i.e., lower layer, insert, upper layer). A transitioning section 1615 having only the upper and lower layers may be disposed adjacent the digits in zones z2,z4. An elongated body 1630 composed of only the lower layer (or the upper and the lower layer) stretching across all five zones may extend between the two transition sections. The length and/or width of the elongated body 1630 may be varied as desired. In use, unibody bridge 1600 may be wrapped around a body part (e.g., arm, shoulder, knee, or some other body part or joint) so that the two ends are disposed on opposite sides of a wound W19 and the digits on either side of the bridge are coupled together via a suture (FIG. 21B).

In at least some embodiments, hemi-bridges may have features, such as openings, to allow for the passage of air and/or liquid therethrough. For example, FIG. 22A is a schematic top view of one example of a hemi-bridge 1700A having openings in the form of slits 1751a that extend parallel to the longitudinal axis of the device. Slits 1751a are arranged in rows as shown, and each row may include one or more slits. In at least some examples, the slits are offset in adjacent rows. Alternatively, a hemi-bridge 1700B may include slits 1751b that are perpendicular to the longitudinal axis of the device (i.e., parallel to the wound edge) and arranged columns, each column having one or more slits. Instead of slits, a hemi-bridge 1700C may include circular apertures 1751c arranged in rows and/or columns. Any of these features (or combinations of them) may be disposed in one of the zones (e.g., limited to one or more locations in the second zone) or in multiple zones (e.g., the second and third zones). Features such as slits or openings in the second zone may allow air to flow therethrough and allow moisture to escape the wound to prevent or reduce the possibility of maceration. It will be understood that these features may be included and combined with any of the embodiments described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A stress dispersing device having a plurality of zones including a first zone, a second zone and a third zone, comprising:
    a lower layer extending across each of the first zone, the second zone and the third zone;
    an upper layer disposed in the first zone and the second zone; and
    an insert having at least one eyelet disposed in the first zone, the insert being sandwiched between the upper layer and the lower layer;
    wherein the first zone includes multiple distinct digits, each digit having a lower layer, an upper layer and an insert.

2. The stress dispersing device of claim 1, wherein the first zone is configured and arranged to elevate a suture above a plane of a patient's skin, and wherein the at least one eyelet includes one eyelet.

3. The stress dispersing device of claim 1, wherein the at least one eyelet includes multiple eyelets arranged in a row parallel with a longitudinal axis of the stress dispersing device.

4. The stress dispersing device of claim 1, wherein the at least one eyelet includes multiple eyelets arranged in a column perpendicular to a longitudinal axis of the stress dispersing device.

5. The stress dispersing device of claim 1, wherein the multiple distinct digits include three digits, each of the three digits having at least one eyelet.

6. The stress dispersing device of claim 1, wherein the third zone includes a plurality of distinct tabs.

7. The stress dispersing device of claim 6, wherein the plurality of distinct tabs includes three tabs of a same length.

8. The stress dispersing device of claim 6, wherein the plurality of distinct tabs includes three tabs, at least one of the tabs being longer than others of the tabs.

9. The stress dispersing device of claim 1, further comprising an adhesive applied to at least one side of the lower layer, and wherein the second zone includes a first portion having a constant width, and a second portion having a gradually decreasing width from the distal end toward the proximal end, the first portion having a plurality of openings.

10. A suture securing device having a plurality of zones including a first zone, a second zone, a third zone, a fourth zone, and a fifth zone comprising:
    a lower layer extending across each of the plurality of zones, the lower layer having an adhesive applied on a bottom thereof;
    an upper layer disposed in the first zone, the second zone, the fourth zone, and the fifth zone; and
    at least one insert having at least one eyelet disposed in the first zone and the fifth zone, the at least one insert being sandwiched between the upper layer and the lower layer;
    wherein the fist zone and the fifth zone each include multiple distinct digits, each digit having a lower layer and an upper layer sandwiching the at least one insert.

11. The suture securing device of claim 10, wherein the multiple distinct digits in the first zone and the fifth zone each include three digits, each digit having at least one eyelet.

12. A system, comprising:
    a stress dispersing wound closure device including a pair of hemi-bridges, each of the pair of hemi-bridges having a plurality of zones including a first zone, a second zone and a third zone, the hemi-bridges including (i) a lower layer extending across each of the first zone, the second zone and the third zone, (ii) an upper layer disposed in the first zone and the second zone, and (iii) an insert having at least one eyelet disposed in the first zone, the insert being sandwiched between the upper layer and the lower layer; and
    a fastening element coupling the pair of hemi-bridges;
    wherein the first zone includes multiple distinct digits, each digit having a lower layer, an upper layer and an insert.

13. The system of claim 12, wherein the multiple distinct digits includes three digits, each digit having at least one eyelet.

14. The system of claim 12, wherein the third zone includes a plurality of distinct tabs.

15. The system of claim 12, wherein the pair of hemi-bridges are similar in shape and size, and are configured to be disposed on opposite sides of a wound and aligned to face one another such that a first insert of a first hemi-bridge is closest to a second insert of a second hemi-bridge.

16. The system of claim 12, wherein the plurality of zones have varying thicknesses, and wherein the first zone is configured and arranged to elevate a suture above a plane of a patient's skin.

17. The system of claim 16, wherein the fastening element is a suture.

\* \* \* \* \*